U.S. Patent Number: 5,531,757
Date of Patent: Jul. 2, 1996

United States Patent
Kensey et al.

[54] METHODS AND STABILIZED INSTRUMENTS FOR PERFORMING MEDICAL PROCEDURES PERCUTANEOUSLY WITHOUT A TROCAR

[76] Inventors: Kenneth Kensey, 8 Hickory La., Chester Springs, Pa. 19425; James Meikle, Jr., 56 Sonia La., Broomall, Pa. 19008; Harold Clupper, 1024 Little Shiloh Rd., West Chester, Pa. 19380; John E. Nash, 145 Oak St., Downingtown, Pa. 19335

[21] Appl. No.: 198,429

[22] Filed: Feb. 22, 1994

Related U.S. Application Data

[63] Continuation-in-part of Ser. No. 35,333, Mar. 19, 1993, abandoned, which is a continuation-in-part of Ser. No. 969,625, Oct. 30, 1992, abandoned.

[51] Int. Cl.⁶ ............................................. A61B 17/34
[52] U.S. Cl. .......................... 606/185; 606/205; 128/793; 604/263
[58] Field of Search ..................... 604/263, 272, 604/22, 902; 128/749, 751–754, 745; 606/205–208.1, 167, 184, 185, 211

[56] References Cited

U.S. PATENT DOCUMENTS

| | | | |
|---|---|---|---|
| 3,469,580 | 9/1969 | Huddy | 604/272 X |
| 4,708,147 | 11/1987 | Haaga | 128/753 |
| 4,877,026 | 10/1989 | de LaForcade | 606/171 |
| 4,923,441 | 5/1990 | Shuler | 604/22 |
| 5,383,886 | 1/1995 | Kensey et al. | 606/185 |

*Primary Examiner*—C. Fred Rosenbaum
*Assistant Examiner*—V. Alexander
*Attorney, Agent, or Firm*—Caesar, Rivise, Bernstein, Cohen & Pokotilow, Ltd.

[57] ABSTRACT

A piercing device for use with an essentially rigid medical instrument having a proximal portion and a distal portion including working means for performing some medical procedure in an internal portion of the body of a living being. The piercing device comprises a guide member having a handle at the proximal end. The guide member comprises an elongated trough shaped, U-shaped, sidewall having an inner surface, and a distal end in the form of a piercing tip. The device is arranged to be held so that the piercing tip can be pierced through the skin and at least a portion of the underlying tissue to form a trough shaped percutaneous puncture. The tissue contiguous with the puncture engages the inner and outer surfaces of the sidewall to form a generally fluid tight interface therebetween. The working means of the instrument can be readily slid along the inner surface of the guide member after the device has formed the percutaneous puncture so that the working means passes through the trough shaped puncture into the being's body. The piercing device is then removed from the percutaneous puncture, leaving the instrument in place with the tissue contiguous with the puncture closely engaging peripheral portions of the instrument at a fluid tight interface so that substantially no fluid leaks out of the interface and so that the working means can be operated to perform the procedure.

35 Claims, 11 Drawing Sheets

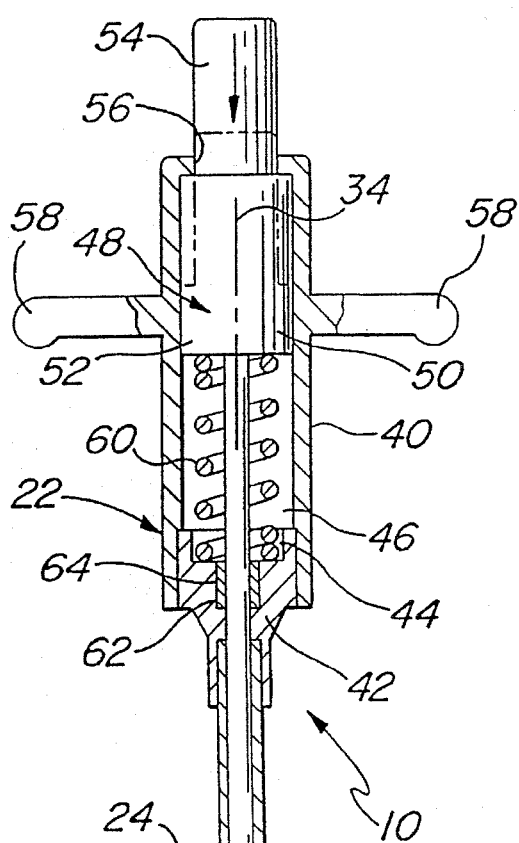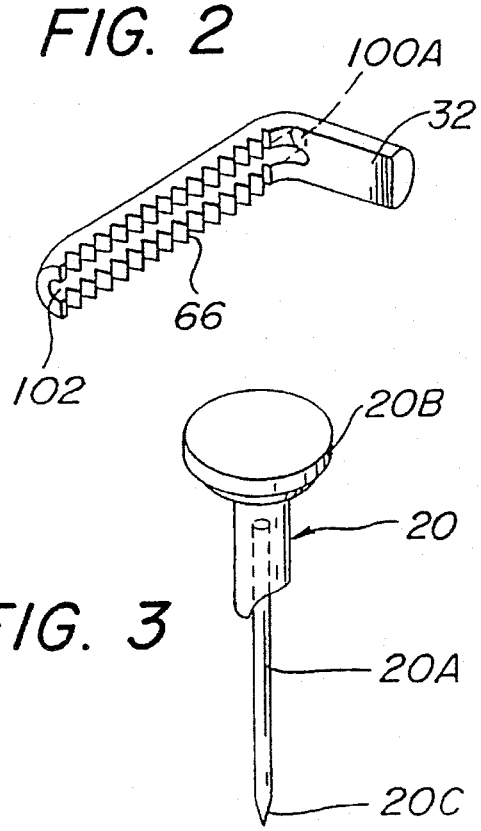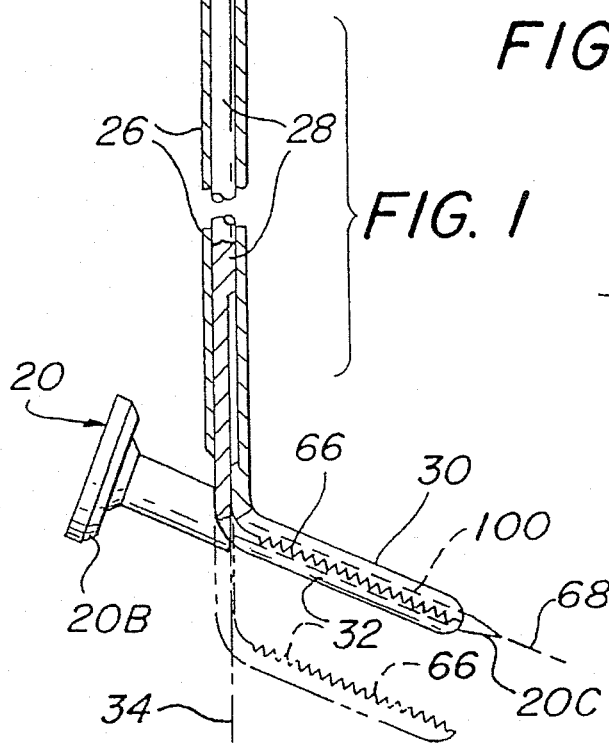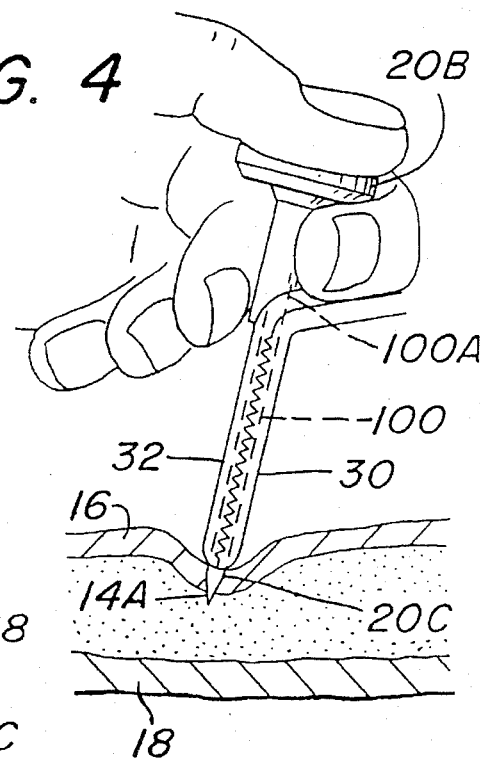

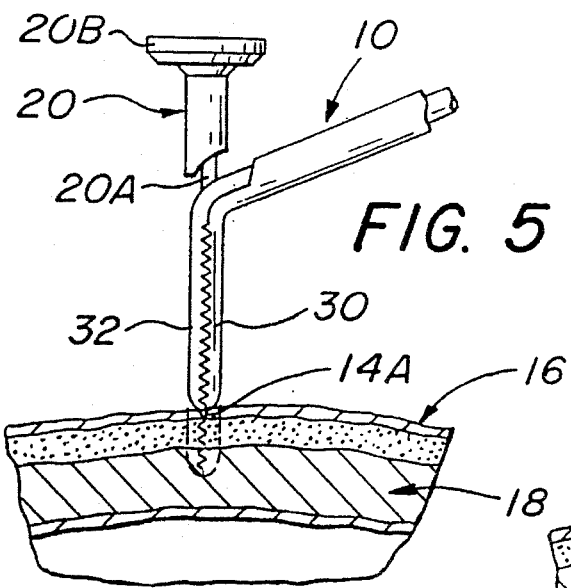
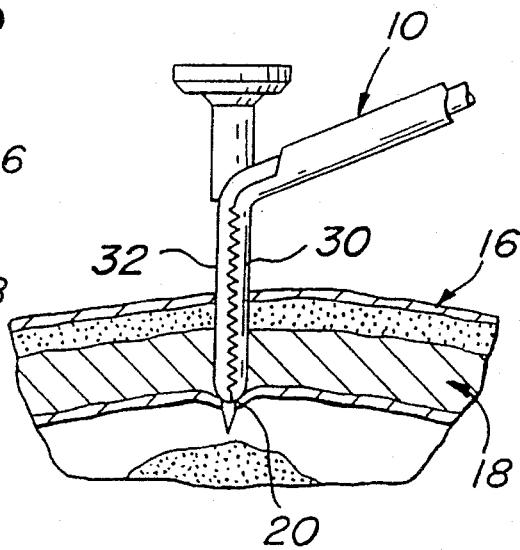
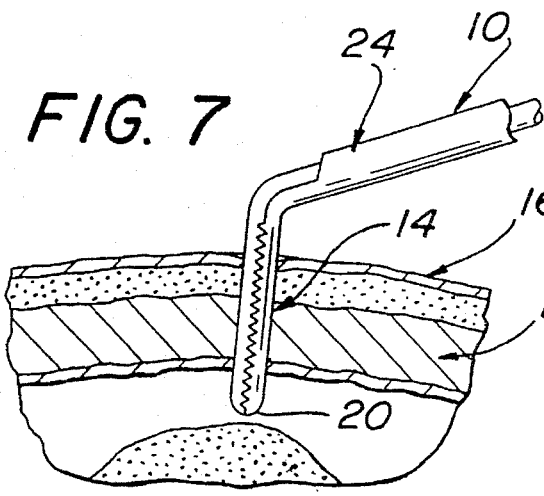
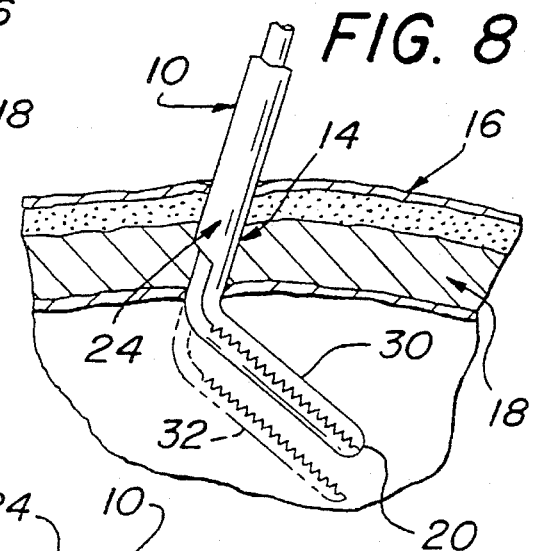
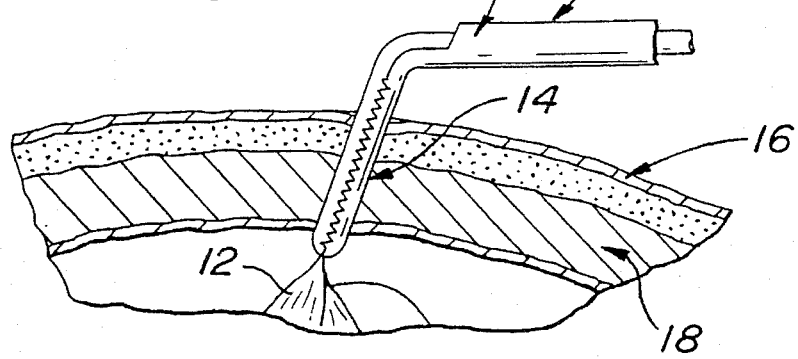

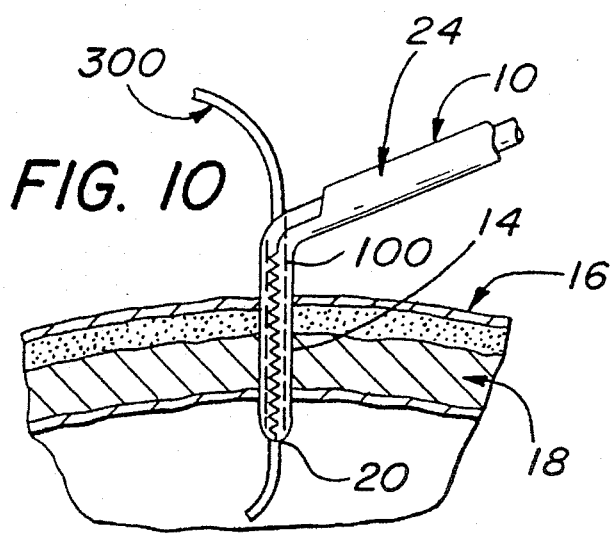
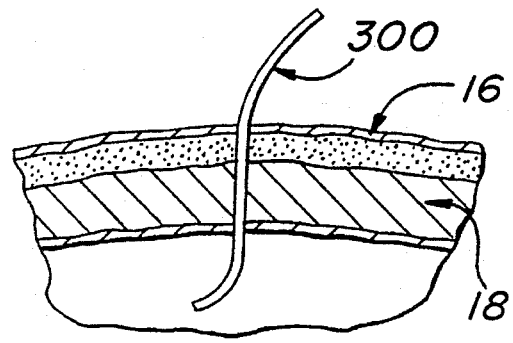
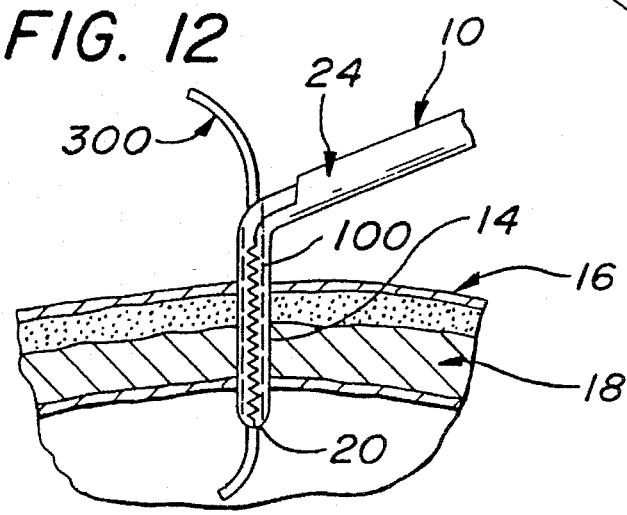

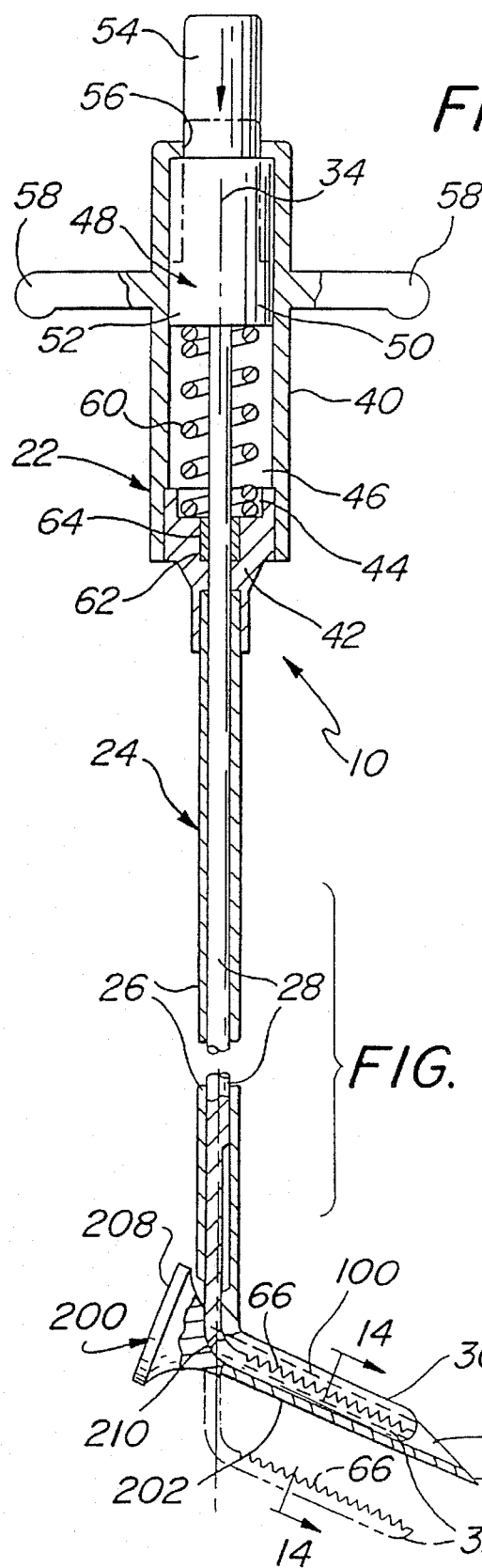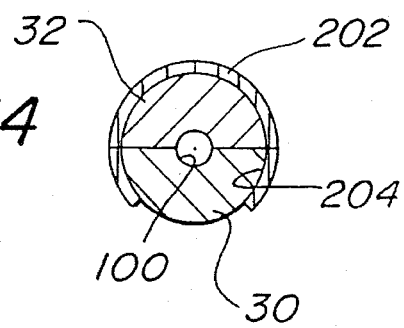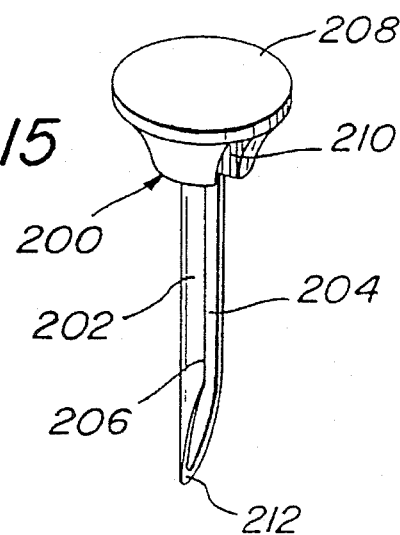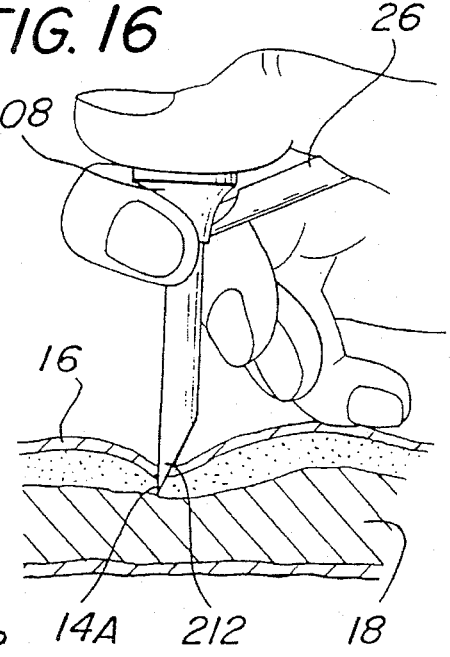

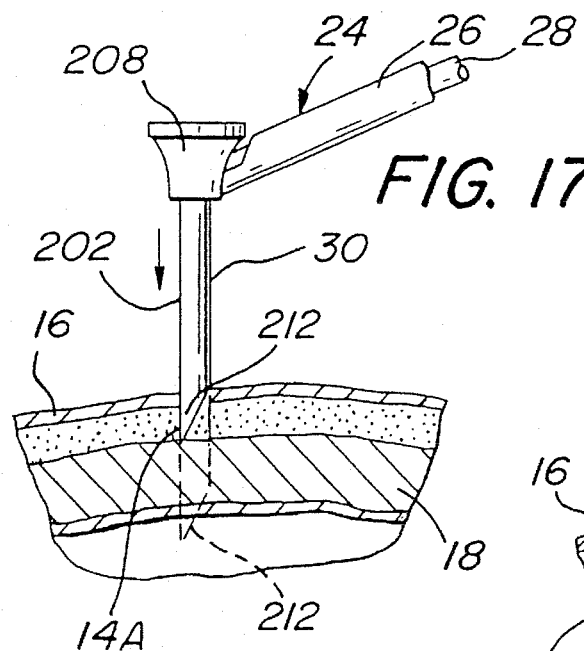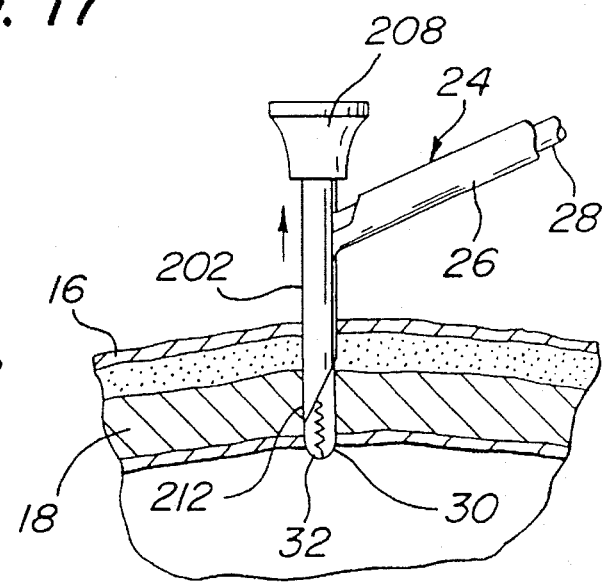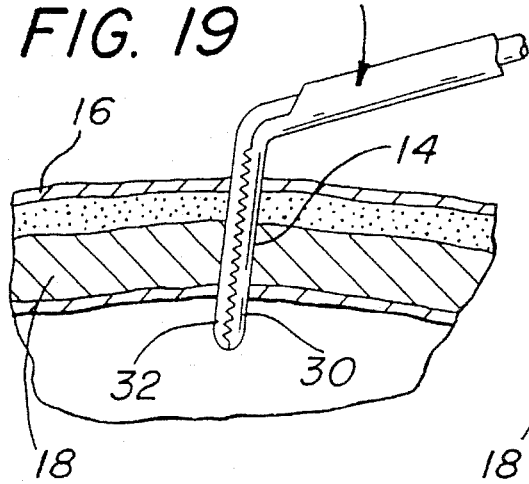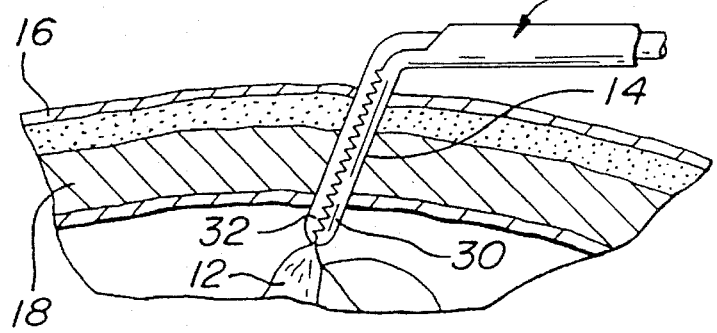

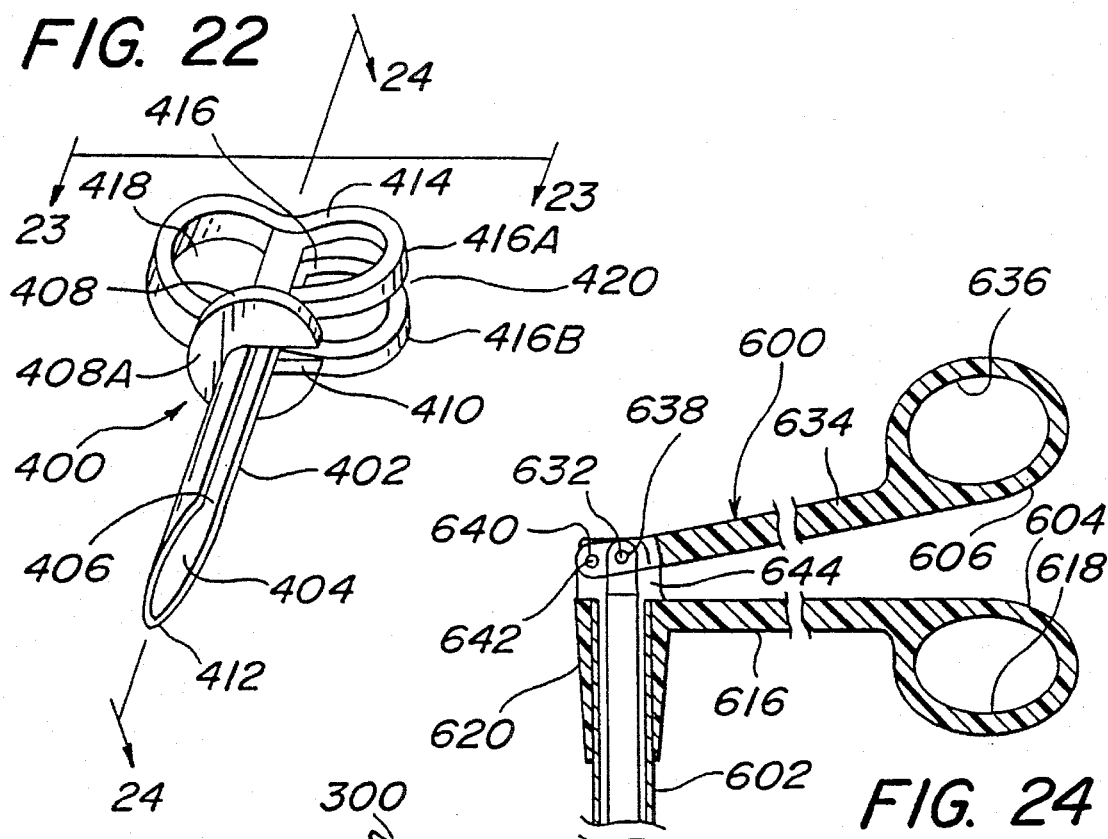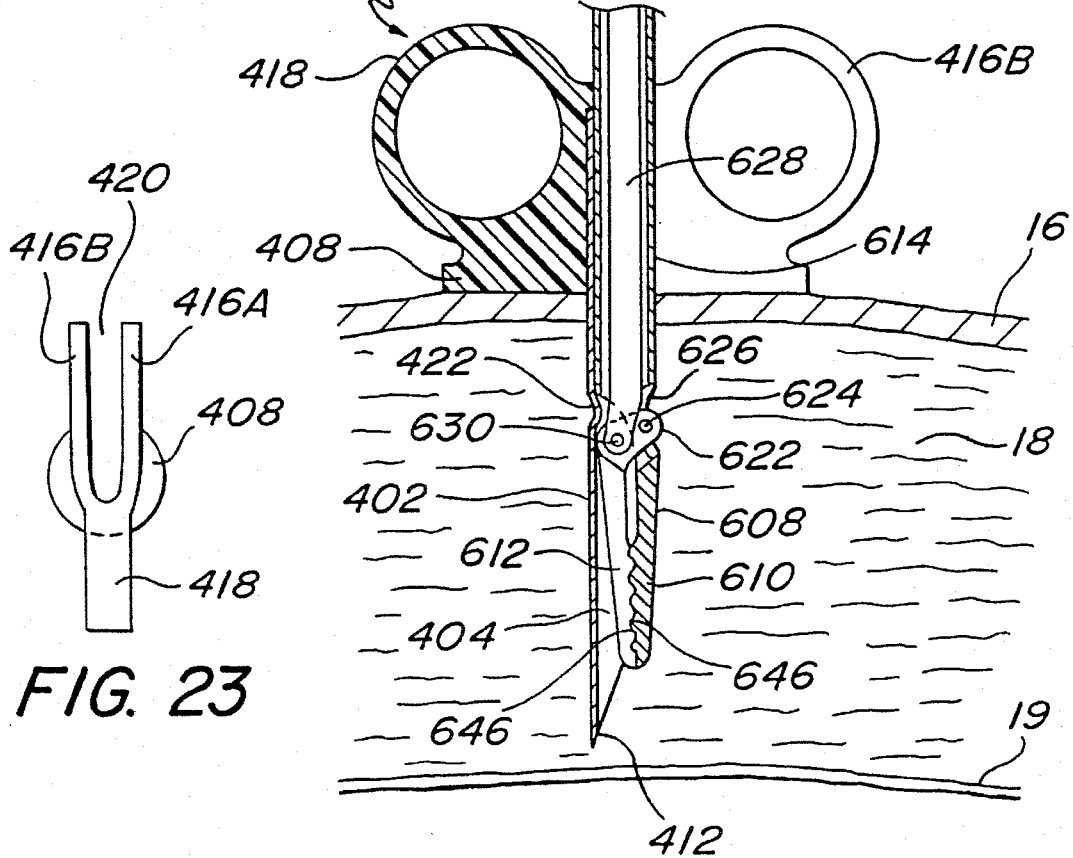

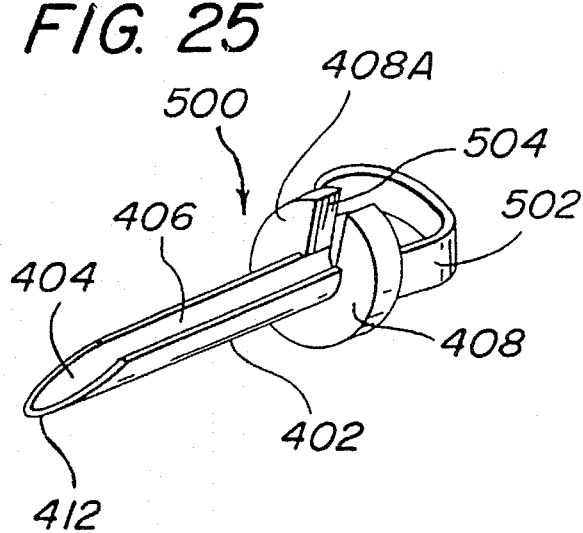
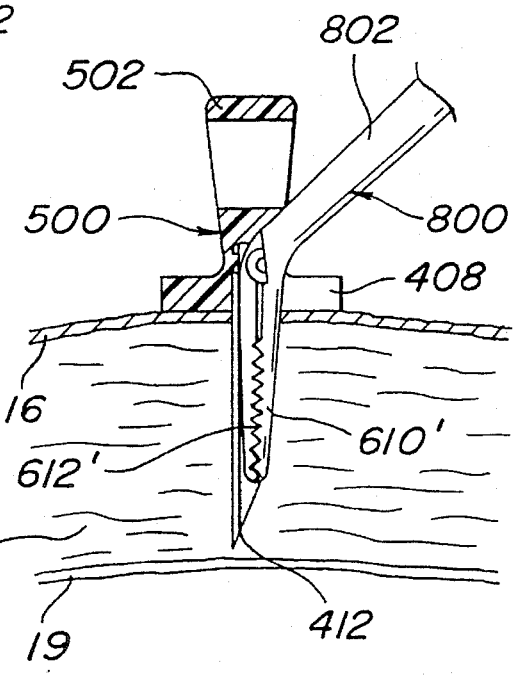
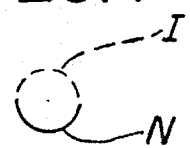
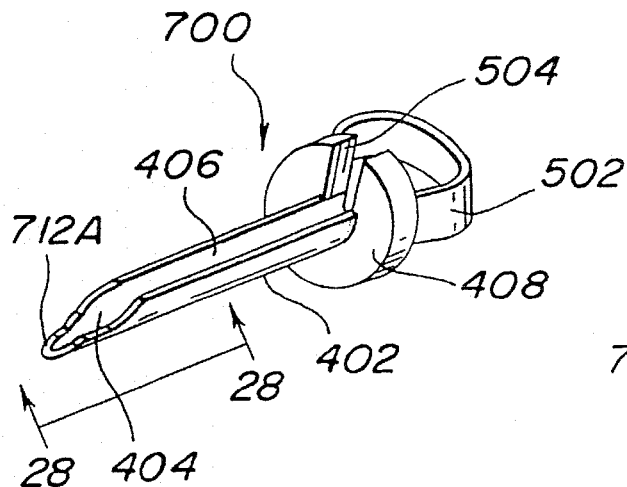
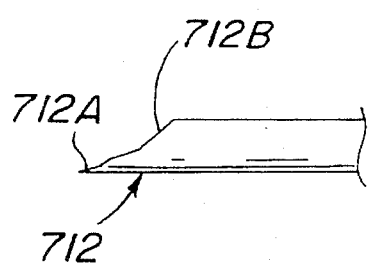
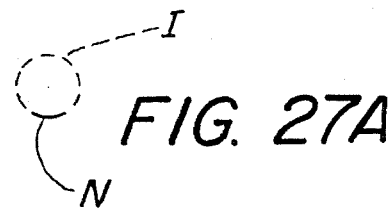

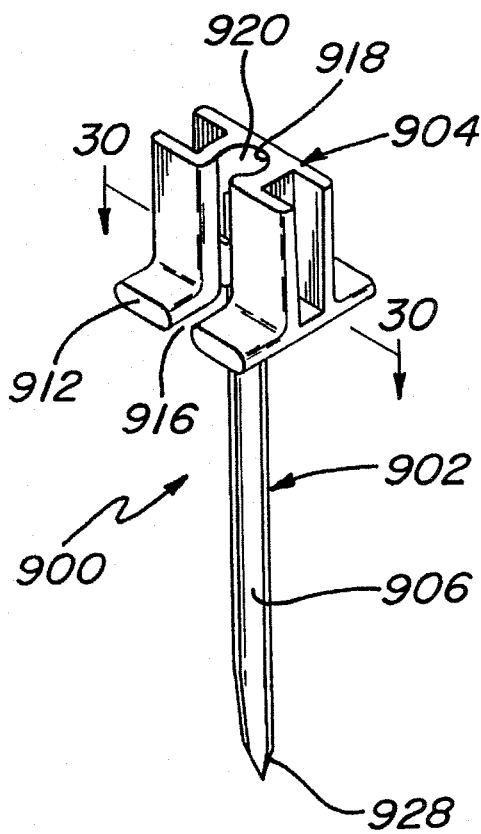
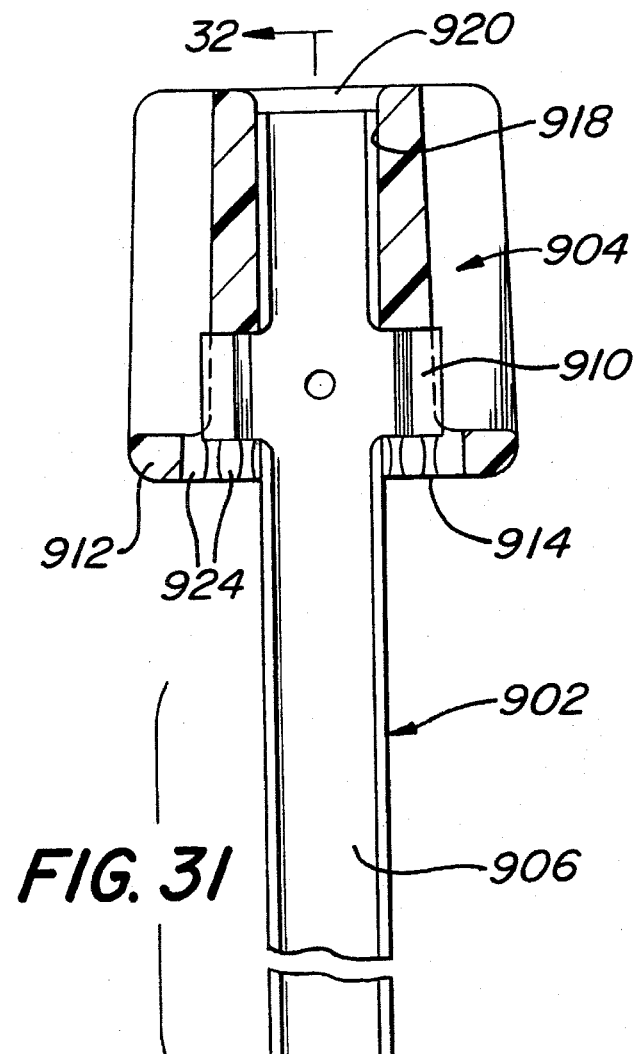
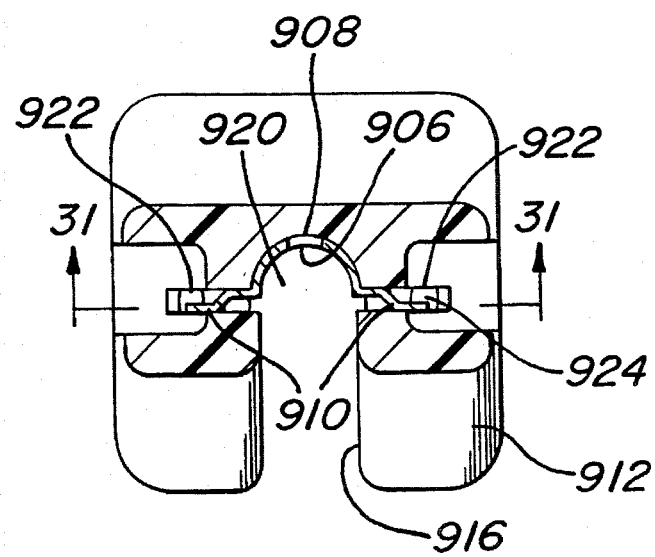
FIG. 29
FIG. 30
FIG. 31

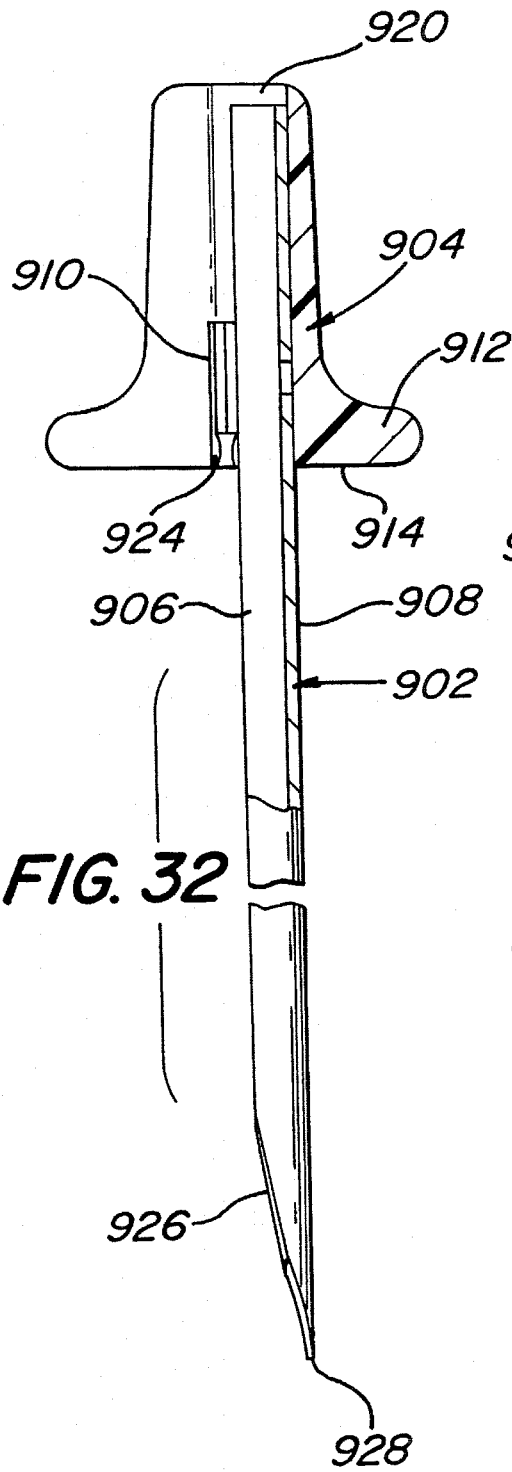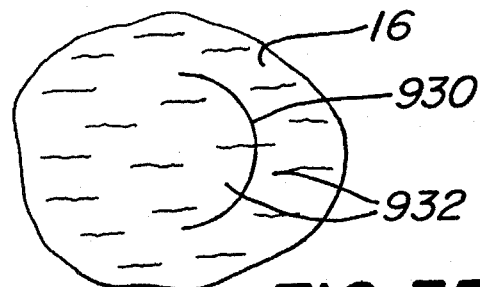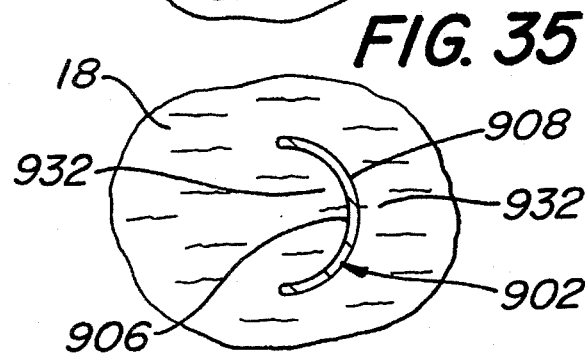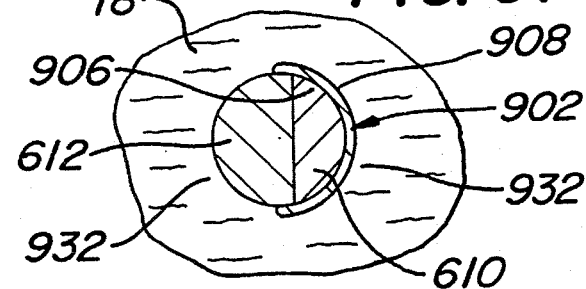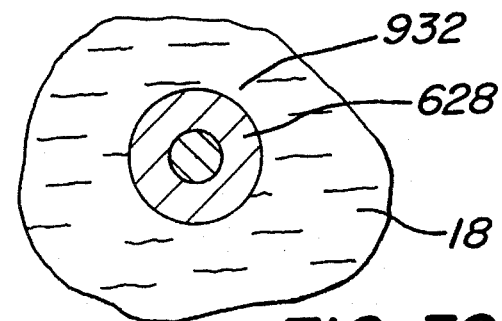

METHODS AND STABILIZED INSTRUMENTS FOR PERFORMING MEDICAL PROCEDURES PERCUTANEOUSLY WITHOUT A TROCAR

SPECIFICATION

This application is a continuation-in-part of U.S. patent application Ser. No. 08/035,333, filed on Mar. 19, 1993, entitled Methods And Stabilized Instruments For Performing Medical Procedures Percutaneously Without A Trocar, now abandoned whose disclosure is incorporated by reference herein and which is assigned to the same assignee as this invention. The Ser. No. 08/035,333 application is, in turn, a continuation-in-part of U.S. patent application Ser. No. 07/969,625, filed on Oct. 30, 1992, now abandoned entitled Methods And Stabilized Instruments For Performing Medical Procedures Percutaneously Without A Trocar, whose disclosure is also incorporated by reference herein and which is assigned to the same assignee as this invention.

This invention relates generally to medical devices and methods of use, and more specifically to devices and methods of use for performing medical procedures within the body of a patient via a small percutaneous incision or puncture and without requiring the use of a trocar to provide access into the patient's body.

Various devices are commercially available for introduction through a trocar into the body of a being to effect some laparoscopic or endoscopic procedure. One typical type of device comprises grasper for grasping and positioning, e.g., reflecting, tissue within the patient's body. Such devices comprise an elongated body member having a distal end at which a pair of pivotable jaws are located and a proximal end at which a pair of pivotable actuating handles are located. The instrument is inserted within the patient's body through a conventional trocar until the pivotable jaws are located adjacent the tissue to be clamped. The actuating handles are then squeezed together to cause the jaws, which are coupled thereto, to grasp the tissue. Other types of trocar introduced devices used heretofore are staplers, biopsy devices, electrocautery devices, suturers, etc.

The patent literature includes various devices to effect some laparoscopic, endoscopic, arthroscopic, or other minimally invasive surgery or procedure, e.g., U.S. Pat. Nos.: 4,662,371 (Whipple et al.); 4,763,669 (Jaeger); 4,872,456 (Hasson); 4,917,100 (Nottke); and 4,963,147 (Agee et al.).

Other medical instruments utilizing jaws or cutting blades are shown in U.S. Pat. Nos.: 984,756 (Frisch); 1,659,112 (Littlejohn); and 4,877,026 (deLaforcade).

While the prior art devices may be suitable for their intended purposes, they never the less leave much to be desired from various standpoints. For example, instruments requiring the use of a trocar for percutaneous introduction typically require that the incision or puncture be sutured after the trocar has been removed. Obviously, this action is time consuming, relatively expensive, and wasteful of personnel resources. Moreover, the making of the incision or puncture sufficiently large for a conventional trocar is somewhat traumatic for the patient, particularly if multiple incisions or punctures are required to effect the percutaneous procedure.

In U.S. Pat. No. 5,318,040, filed on Aug. 27, 1992, entitled Instruments And Methods For Performing Medical Procedures Via Small Percutaneous Incisions Or Punctures Without Using A Trocar, which is assigned to the same assignee as this invention, and whose disclosure is incorporated by reference herein there is disclosed and claimed various devices and methods for effecting medical procedures via very small, self-sealing, percutaneous incisions or punctures without using a trocar to expedite the procedures, conserve medical resources, minimize trauma to the patient. To achieve that end the apparatus of that invention has a proximal portion and a distal portion, with the distal portion including a sharp piercing end for forming a small percutaneous incision or puncture to enable the distal portion be inserted into the being's body to a desired internal position without the use of a trocar or other introducing device. The distal portion of the apparatus is elongated and has a longitudinal axis. In one embodiment, an actuatable mechanism, e.g., a pair of moveable jaws, is located at the distal portion and is arranged to be pivoted outward laterally of the longitudinal axis for engagement with tissue located at the operative site to perform some operation, e.g., clamping. The actuatable mechanism is actuated by the proximal portion of the apparatus. In another embodiment, the jaws are permanently extended outward of the longitudinal axis. The piercing tip may take various forms. In one form it is pivotable to enable it to be moved from an extended position to a retracted position after it has pierced the skin and underlying tissue and is within the interior of the patient's body. In another form the piercing tip is removable so that it can be removed after it has pierced the skin and underlying tissue and is within the interior of the patient's body.

In U.S. Pat. No. 5,383,886 filed on Oct. 13, 1992, entitled Methods And Instruments For Performing Medical Procedures Percutaneously Without A Trocar, which is assigned to the same assignee as this invention and whose disclosure is incorporated by reference herein there is disclosed and claimed methods and apparatus which achieve the ends of the invention of the aforementioned U.S. Pat. No. 5,318,040 yet which are somewhat simpler. While the devices of that patent application are suitable for their intended purposes, in some applications they may still leave something to be desired from the standpoint of ease of use.

In the aforementioned parent application there is disclosed and claimed various devices and methods for effecting medical procedures via very small, self-sealing, percutaneous incisions or punctures without using a trocar to expedite the procedures, conserve medical resources, minimize trauma to the patient. In particular, in three embodiments of the invention a piercing device is provided for use with a medical instrument for performing some medical procedure in an internal portion of the body of a living being from outside the body of the being. The instrument has a proximal portion and a distal portion including working means. The three disclosed piercing devices each comprise an elongated tubular member and a handle member secured thereto. The tubular member has a hollow interior, a distal end portion terminating in a piercing tip, a longitudinal axis, and a slot extending along at least a portion of the elongated tubular member from the distal end portion. The handle member is arranged to be held so that the piercing tip can be brought into engagement with the skin over said internal portion and extended through the skin and at least a portion of underlying tissue to form a trough shaped puncture, e.g., a puncture whose shape is essentially the same as a transverse section of the distal end portion of the tubular member. The hollow interior of the piercing member arranged to slidably receive the distal portion of the instrument therein so that the working means can be passed through the puncture into the internal portion, whereupon the piercing device can be slid off of the instrument to leave the working means within the interior portion to perform the procedure while the proximal portion of the instrument is located outside of the body of the being.

It has been determined that those piercing devices and their method of use as set forth in the parent application Ser. No. 08/035,333, now abandoned, leaves something to be desired from the standpoint of simplicity and ease of use.

Various prior art devices have been disclosed in the literature for forming trough shaped puncture. For example, U.S. Pat. No. 1,573,681 (Daireaux) discloses a piercing device comprising an elongated arcuate (half round) sidewall mounted on a handle for forming a trough shaped percutaneous puncture. However, it fails to disclose a guide member (i.e., the sidewall) being shaped to enable working means of an instrument to be slid along the inner surface of the arcuate sidewall after the device has formed a percutaneous puncture.

U.S. Pat. No. 3,359,978 (Smith) discloses a guide needle for a flexible catheter comprising an elongated tube whose distal end is either half round or V-shaped. A handle is mounted on the tube. This patent fails to disclose a guide member having a trough shaped sidewall to form a trough shaped percutaneous puncture extending from the outside of the body of the being to an interior point within the being's body.

U.S. Pat. No. 5,186,178 (Yeh et al.) discloses a biopsy device which includes a crescent shaped piercing blade. However, it fails to disclose a guide member (i.e., the crescent shaped blade) being constructed to enable working means of an instrument to be slid along its inner surface after it has formed a percutaneous puncture.

British Patents Nos. 904,237 and 1,437,621 are somewhat similar in that they disclose the combination of a trough shaped, e.g., slotted, needle and a flexible catheter for percutaneous insertion into a body lumen, e.g., a vein. However, these references do not show a device for use with an essentially rigid medical instrument. Moreover, the catheter (e.g., the "instrument") inserted in the trough shaped needle is fixedly held in place during the insertion procedure.

Canadian Patent No. 628,292 is similar in construction and operation to the structures of the two above identified British patents in that the catheter is fixedly secured within the trough shaped needle during the insertion procedure.

PCT Application WO 90/13330 discloses a "punction instrument" consisting of a groove shaped perforating lancet having a curved tubular section at its distal end shaped like the prow of a boat. However, this reference doesn't disclose any means for forming a trough shaped percutaneous puncture extending from the outside of the body of the being to an interior point within the being's body.

In an article entitled An Introducer For Plastic Cannulae appearing on page 435 of the Feb. 23, 1952 issue of the British Medical Journal there is disclosed an introducer device for introducing a flexible intravenous cannula into a vein. The introducer comprises a member having a distal portion in the form of a U-shaped member having a sharpened free end. The U-shaped portion supports the flexible cannula therein with the sharpened end of the introducer extending beyond the end of the cannula. The introducer is not arranged for use with an essentially rigid medical instrument. Moreover, the cannula is fixedly held in place during the insertion procedure.

OBJECTS OF THE INVENTION

Accordingly, it is a general object of this invention to provide methods and instruments which overcomes the disadvantages of the prior art.

It is another object of this invention to provide methods and apparatus for accomplishing medical procedures by piercing through internally supported tissue of a patient in a stabilized manner to form one or more percutaneous incisions or punctures which are very small to minimize trauma to the patient.

It is another object of this invention to provide methods and apparatus for accomplishing medical procedures within the body of a being by providing a device for use with an instrument to pierce through the skin and a portion of underlying tissue to form a nick and to thereafter use the instrument itself to pierce through any underlying tissue to form a percutaneous incision or puncture without the use of a trocar or other introducing instrument.

It is another object of this invention to provide methods and apparatus for accomplishing medical procedures within the body of a living being by providing a device for use with an instrument to piercing through the skin and a portion of underlying tissue to form a nick of a predetermined depth and to thereafter use the instrument itself to pierce through any underlying tissue to form a percutaneous incision or puncture without the use of a trocar or other introducing instrument.

It is another object of this invention to provide methods and apparatus for accomplishing medical procedures within the body of a living being by providing a device for use with an instrument piercing through the skin and a portion of underlying tissue to form a nick of a predetermined depth and to thereafter use the instrument itself to pierce through any underlying tissue to form a percutaneous incision or puncture without the use of a trocar or other introducing, and wherein the incision or puncture is very small to minimize trauma to the patient.

It is another object of this invention to provide methods and apparatus for accomplishing medical procedures within the body of a living being by providing a device for use with an instrument to pierce through the skin and a portion of underlying tissue to form a nick of a predetermined depth and to thereafter use the instrument itself to pierce through any underlying tissue to form a very small percutaneous incision or puncture through which the instrument extends for operation without the use of a trocar or other introducing instrument.

It is another object of this invention to provide a device and methods of use for forming a percutaneous puncture in a living being, through which puncture a medical instrument can be extended and which overcomes the disadvantages of the prior art.

It is another object of this invention to provide a simple device for forming a percutaneous puncture in the body of a living being through which puncture a medical instrument can be extended.

It is another object of this invention to provide a device for forming a percutaneous puncture in the body of a living being to be left in place therein to form a self-sealed portal through which a medical instrument can be extended.

It is another object of this invention to provide a device for forming a percutaneous puncture in the body of a living being to guide a instrument therethrough and then be removed leaving the instrument in place to perform a procedure within the body of the being.

It is another object of this invention to provide a device for use on an instrument extending through a percutaneous puncture in the body of a living being so that the instrument can be removed and the device left in place to form a portal for use by another instrument to gain access through the percutaneous puncture to perform a procedure within the body of the being.

It is another object of this invention to provide methods for forming a percutaneous puncture through which an instrument can be extended to perform a procedure within the body of a living being.

It is another object of this invention to provide methods for establishing a portal in a percutaneous puncture so that an instrument can be extended through the portal.

It is another object of this invention to provide methods for establishing a portal in a percutaneous puncture in the body of a living being so that an instrument can be extended through the portal and then the portal removed leaving the instrument extending through the percutaneous puncture to perform a procedure within the body of the being.

It is another object of this invention to provide methods for using a portal to remove an instrument extending through a percutaneous puncture in the body of a living being so that the portal can be left in place to provide access for another instrument therethrough.

It is another object of this invention to provide methods for using a portal to remove an instrument extending through a percutaneous puncture in the body of a living being so that the portal can be left in place and be self-sealed to provide access for another instrument therethrough.

SUMMARY OF THE INVENTION

These and other objects of this invention are achieved by providing methods and apparatus for performing various types of medical procedures in an interior portion of the body of a living being from outside the body of the being via a small percutaneous incision or puncture and without using a trocar or other means to hold the incision or puncture open.

One embodiment of the apparatus is an instrument having a proximal portion, a distal portion, working means, and coupling means. The proximal portion of the instrument is arranged to be held outside the body of the being. The distal portion of the instrument comprises a second tip, and an extendable and retractable elongated piercing member forming a first tip mounted thereon. The first tip is sharp for piercing through the skin to form a very small nick when the piercing member is in an extended position. The second tip of the instrument has a surface arranged to engage and be extended through the nick and through the underlying tissue to form the percutaneous incision or puncture upon the application of force to the instrument, whereupon the distal portion and the working means passes through the incision or puncture into the interior portion without the use of a trocar or other introducing means. Accordingly, the working means is located at a desired position within the interior portion of the being's body.

In accordance with one method aspect of this invention the piercing member is arranged to be retracted either prior to the instrument's second tip entering into the interior of the being's body, e.g., prior to entering the insufflated abdomen, or afterward but prior to the operation of the instrument's working means.

The surface of the second tip is sufficiently blunt so as not to present a hazard to tissue or organs located within the interior portion of the being's body.

In accordance with one preferred embodiment of the invention the piercing member includes a portion arranged to be held in one hand of the user while the proximal portion of the instrument is held in the user's other hand during the formation of the percutaneous incision or puncture to facilitate that action.

The coupling means is coupled to the working means and to the proximal portion to effect the operation of the working means via the proximal portion.

In accordance with another aspect of this invention there is provided a piercing device for use with an essentially rigid medical instrument having a proximal portion and a distal portion including working means for performing some medical procedure in an internal portion of the body of a living being from outside the body of the being. The piercing device comprises a guide member and a head portion. The guide member comprises an elongated trough shaped sidewall having an inner surface defining a trough shaped recess, an outer surface, a distal end portion, and a proximal portion. The distal end portion comprising a piercing tip. The proximal portion of the guide member is secured to the head portion.

The piercing device is arranged to be held by the head portion so that the piercing tip can be brought into engagement with the skin over the internal portion and extended through the skin and at least a portion of the underlying tissue to form a trough shaped percutaneous puncture extending from the outside of the body to a point within the body, with the tissue contiguous with the puncture engaging both of the inner and outer surfaces of the sidewall to form a generally fluid tight interface therebetween.

The piercing device serves as a portal to the internal portion of the body. To that end the guide member is shaped to enable the working means of the instrument to be readily slid along the inner surface of the guide member after the piercing device has formed the percutaneous puncture, so that the working means passes through the trough shaped puncture into the internal portion, whereupon the piercing device can be removed from the percutaneous puncture. The instrument is left in place extending through the percutaneous puncture, with the tissue contiguous with the puncture closely engaging peripheral portions of the instrument at a fluid tight interface so that substantially no fluid leaks out of the interface. The instrument can then be operated and so that the working means performs a desired procedure within the body of the being.

In accordance with another method aspect of the invention another elongated guide member having a longitudinal axis and comprising an elongated trough shaped sidewall having an inner surface, an outer surface, a proximal portion, and a distal end portion is provided after the instrument has performed the procedure. The other elongated guide member is then located on the instrument so that the inner surface of the other guide member is on said instrument while the instrument is extended through the trough shaped opening. The other guide member is slid longitudinally along the instrument so that the distal end portion of the other guide member enters the trough shaped percutaneous puncture and into the internal portion in the being's body. Thereafter the instrument is slid in a proximal along the inner surface of the other guide member to remove the instrument from the percutaneous puncture. The other guide member is left in place to form a portal, with the tissue contiguous with the puncture engaging portions of said inner and outer surfaces of the other guide member to form a fluid tight interface therebetween.

In accordance with a further method aspect of this invention another instrument is provided for extension through the portal. The other instrument, which may be the same instrument as used previously or another, basically comprises a proximal portion and a distal portion including working means for performing some procedure within the body of the being. The distal portion of the other instrument is then slid in a distal direction along the inner surface of the other guide member, i.e., the portal, to be guided thereby through the percutaneous puncture, whereupon the working means passes therethrough into the internal portion. The other guide member can then be removed from the percutaneous puncture and the other instrument operated to cause its working means to perform the desired procedure within the internal portion of the being's body.

BRIEF DESCRIPTION OF THE DRAWINGS

Other objects and many of the attendant advantages of this invention will readily be appreciated as the same becomes better understood by reference to the following detailed description when considered in connection with the accompanying drawings wherein:

FIG. 1 is a longitudinal sectional view of an instrument constructed in accordance with this invention;

FIG. 2 is an enlarged isometric view of one of the jaws forming the distal end of the instrument shown in FIG. 1;

FIG. 3 is an enlarged isometric view of the piercing means portion of the instrument shown in FIG. 1;

FIGS. 4–9 are illustrations showing the sequence of use of the instrument of FIG. 1 for effecting the reflection of a lobe of the liver to expose the gall bladder;

FIGS. 10–12 are illustrations showing a sequence of use of the instrument of FIG. 1 for placing a guide wire through the percutaneous incision or puncture using the instrument shown in FIGS. 4–9, removing that instrument from the incision or puncture leaving the guide wire in place, and then using that guide wire to guide another instrument through the percutaneous incision or puncture into the interior portion of the being's body;

FIG. 13 is a longitudinal sectional view of an alternative embodiment of an instrument constructed in accordance with this invention;

FIG. 14 is an enlarged sectional view taken along line 14—14 of FIG. 13;

FIG. 15 is an enlarged isometric view of a piercing device forming the piercing means portion of the instrument shown in FIG. 13;

FIGS. 16–21 are illustrations showing the sequence of use of the instrument of FIG. 13 for effecting the reflection of a lobe of the liver to expose the gall bladder;

FIG. 22 is an isometric view of an alternative embodiment of the piercing device shown in FIG. 15;

FIG. 23 is an end view of the device shown in FIG. 22 taken along line 23—23;

FIG. 24 is an enlarged illustration showing the use of the piercing device shown in FIG. 22 on a conventional type of medical instrument for forming a percutaneous incision or puncture through the abdominal wall and without the use of a trocar;

FIG. 25 is an isometric view of an alternative embodiment of the piercing device shown in FIG. 22;

FIG. 25A is a plan view of the opening in the skin and underlying tissue created by the devices shown in FIGS. 22 and 25;

FIG. 26 is an illustration showing the use of the piercing device shown in FIG. 25 on another type of medical instrument for forming a percutaneous incision or puncture through the abdominal wall and without the use of a trocar;

FIG. 27 is an isometric view of an alternative embodiment of the piercing device shown in FIG. 25;

FIG. 27A is a plan view of the opening in the skin and underlying tissue created by the device shown in FIG. 27;

FIG. 28 is a side elevational view of the distal end of the device shown in FIG. 27 taken along line 28—28.

FIG. 29 is an isometric view of a most preferred embodiment of a piercing device constructed in accordance with this invention;

FIG. 30 is an enlarged sectional view taken along line 30—30 of FIG. 29;

FIG. 31 is a sectional view taken along line 31—31 of FIG. 30;

FIG. 32 is a sectional view taken along line 32—32 of FIG. 31;

FIG. 34 is an enlarged plan view of the trough shaped percutaneous puncture formed by the piercing device of FIG. 29 after the piercing device has been removed therefrom;

FIG. 35 is an enlarged sectional view taken along line 35—35 of FIG. 33;

FIG. 37 is an enlarged sectional view taken along line 37—37 of FIG. 36;

FIG. 39 is an enlarged sectional view taken along line 39—39 of FIG. 38;

DETAILED DESCRIPTION OF THE PREFERRED EMBODIMENTS

Figure 33:
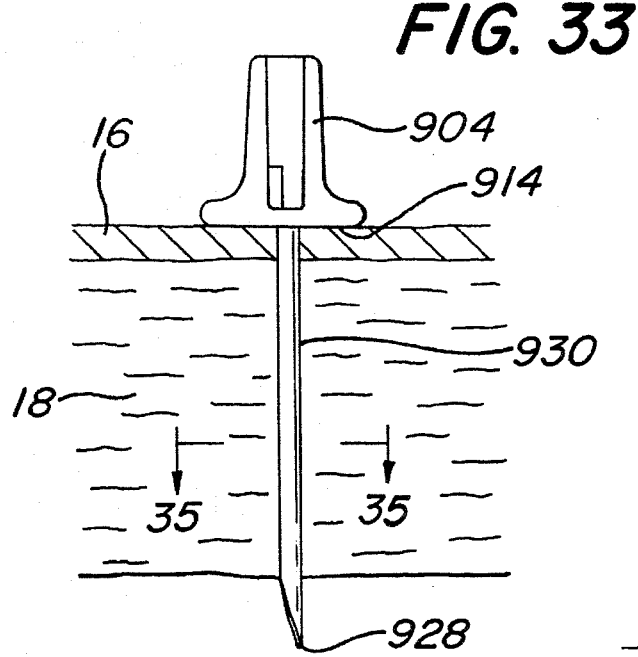
FIG. 33 is an illustration showing the use of the piercing device of FIG. 29 after it has been extended through the skin and underlying tissue into an insufflated abdomen to serve as a portal through which an instrument may be extended into the insufflated abdomen.

Referring now in greater detail to the various figures of the drawings wherein like reference characters refer to like parts there is shown in FIGS. 1 and 13 two instruments 10 for accomplishing some of the methods of this invention. Each of the instruments 10 are of identical construction, except for a piercing member (to be described later). Each instrument is arranged to be extended, without use of any trocar or similar device, through the skin and underlying internally supported tissue of the body of a living being to perform some procedure therein, e.g., for grasping internal tissue to hold it in place or reflect it to a different position during endoscopic, laparoscopic, arthroscopic, or other similar percutaneous procedures.

In fact, each of the instruments 10 is arranged to form the percutaneous incision or puncture, with the size of the percutaneous incision or puncture being sufficiently small that it seals itself upon removal of the instrument from it. To that end each of the instruments 10 includes an elongated portion (to be described later) of very small cross sectional area, e.g., 0.109 inch (2.77 mm) or less, at the distal end thereof for forming the percutaneous incision or puncture so that the distal end of the instrument having working means thereon is located within the body of the patient at a desired situs.

In order to provide a starting point for the incision or puncture and to facilitate its formation, the instrument 10 of FIG. 1 includes one embodiment of a piercing member 20 mounted at the distal end of that instrument. In a similar manner the instrument 10 of FIG. 13 includes another embodiment of a piercing member 200 mounted at the distal of that instrument. The piercing members 20 and 200 will be described in detail later. Suffice it for now to state that the each piercing member 20 and 200 includes a small diameter sharply pointed distal end and is mounted within (in the case of member 20) or on (in the case of member 200) the distal portion of the instrument so that it can be moved to an extended position which can be brought into engagement with the skin of the patient overlying the internal situs at which the procedure is to be conducted to form a small nick or cut in the skin. Once that has been accomplished the piercing member may be retracted into the distal end of the instrument or may be left extended or may be removed entirely from the instrument.

The distal portion of the elongated portion of the instrument is in the form of a pair of jaws (also to be described later) which conjoin so that the surfaces of their distal free ends together form a tissue engagement surface. The engagement surface is somewhat rounded and blunt and is arranged to be brought into engagement with the nick in the skin and forced therethrough and through the underlying tissue to form the percutaneous incision or puncture, as will be described later.

The jaws extend outward of the longitudinal axis of the instrument for grasping adjacent internal tissue, yet do not interfere with the passage of the elongated portion of the instrument through the percutaneous incision or puncture to the operative situs.

It must be pointed out at this juncture that the instrument 10 disclosed and described herein is merely exemplary of various types of instruments which can be constructed in accordance with the teachings of this invention. Thus, instruments can be constructed for effecting other types of procedures, such as resecting, dissecting, extracting, ablating, cauterizing, suturing, stapling, etc., which are to be carried out through a very small percutaneous incision or puncture in order to minimize patient trauma and to facilitate healing.

The instruments 10 of this invention are similar to the instrument disclosed in the aforementioned U.S. Pat. No. 5,383,886 filed on Oct. 13, 1992 entitled Methods And Instruments For Performing Medical Procedures Percutaneously Without A Trocar, except for the construction of the extendable/retractable piercing tip 20.

In the illustrations of FIGS. 4–9 and in the illustrations of FIGS. 16–21 there is shown the distal end of the instruments 10 of FIG. 1 and 13, respectively, being used to reflect a lobe of a patient's liver 12 (FIGS. 9 and 21) via a percutaneous incision or puncture 14 extending through the skin 16 and underlying tissue 18. In order to expedite the passage of each instrument 10 through the skin 16 and underlying tissue 18 to form the small percutaneous incision or puncture 14, such tissue should be supported internally. In cases where the instrument 10 has to extend into the abdomen the internal support for the tissue to be pierced can be readily achieved by insufflating the abdomen with a gas, as is conventional during laparoscopic surgery today. In cases where the surgery is to be performed within the chest, insufflation or other artificial support should not be necessary since the ribs should provide adequate internal support to enable the instrument to form the percutaneous incision or puncture between adjacent ribs.

As mentioned earlier the instruments 10 are identical in construction except for the piercing means 20 and 200 utilized with them. Thus, the same reference numbers will be used to describe like parts of the instruments 10 of FIGS. 1 and 13. To that end and referring now to FIG. 1 it can be seen that the instrument 10, basically comprises housing or body portion 22 from which an elongated tubular sleeve assembly 24 extends. The sleeve assembly comprises an elongated sleeve 26, and an elongated rod or shaft 28 slidably mounted therein. The sleeve assembly 24 may be straight (as shown) or may be curved. In any case the distal end portion of the sleeve 26 includes an angularly oriented extension forming a jaw 30. In a similar manner the distal end portion of the shaft 28 includes an angularly oriented extension forming a jaw 32. The jaws are arranged to be slid with respect to each other parallel to the longitudinal axis 34 of the sleeve and rod so that then can be opened and closed.

It must be pointed out at this juncture that the use of the term "axis" in this application is in the broadest possible sense and context, and, hence, is not limited to a straight line, but can be a line of any shape, e.g., a curved line, since the sleeve assembly 24 need not be straight.

When the jaws 30 and 32 are completely closed, such as shown by the full lines in FIG. 1, they abut each other, whereupon the outer periphery of the conjoined jaws is substantially circular and of very small cross sectional area. Moreover, as noted earlier, the distal end of each jaw is somewhat rounded, and when the jaws are conjoined they form the heretofore identified tissue engagement surface. It is in the conjoined jaw configuration that the instrument 10 is used to pierce through the nick formed in patient's skin 16 by the piercing tip 20 so that upon the application of a force on the instrument the tissue engagement surface passes through the underlying tissue 18 to locate its jaws 30 and 32 within the body of the patient at the desired situs (as will be described later).

In accordance with one aspect of this invention the tissue engagement surface of the instrument can pass through the nick formed by the piercing member 20 and through the underlying internally supported tissue 18 upon the application of a small manual force by the surgeon on the instrument. Moreover, that surface is sufficiently blunt so that it will not pose a hazard to internally located tissue, e.g., tissue within the insufflated abdomen.

In accordance with a preferred embodiment of this invention the outside diameter of the sleeve assembly 24 is very small, e.g., 0.109 inch (2.77 mm) or less, so that the formation of the percutaneous puncture or incision 14 produced by the instrument 10 is very small and self-sealing. By self-sealing it is meant that the puncture or incision will close and seal itself almost immediately after the instrument is withdrawn therefrom and without requiring suturing, taping, or other artificial sealing means.

The body 22 of the instrument 10 basically comprises a hollow cylindrical housing 40 fixedly connected by a connector 42 to the proximal end of the sleeve 26. The housing 40 has a cylindrical interior cavity 46 in which a plunger assembly 48 is located. The plunger assembly is connected to the proximal end of the shaft 28 and serves as the means for sliding the shaft 28 within the sleeve 26 along axis 34 to effect the opening and closing of the jaws 30 and 32.

The plunger assembly 48 basically comprises a rod-like plunger element 50 having a distal end 52 at which the proximal end of the shaft 28 is fixedly secured. The outside diameter of the plunger element 50 is just slightly less than the inside diameter of the hollow interior 46 of the housing 40 so that the plunger element can be slid longitudinally therethrough. The proximal end of the plunger element 50 is in the form of a cap or button 54 which extends through an opening 56 at the proximal end of the housing 40.

The housing 40 includes a pair of tabs 58 projecting perpendicular to the longitudinal axis 34 of the instrument 10. A helical compression spring 60 is located within the hollow interior 46 of the housing 40 interposed between the distal end 52 of the plunger element 50 and an annular recess 44 in the inner surface of the connector 42. The spring 60 surrounds the proximal portion of the shaft 28 and serves to bias the plunger element 50 toward the full line position shown in FIG. 1. In this orientation the jaws 30 and 32 of the instrument 10 are fully closed and the instrument arranged to form the percutaneous incision or puncture 14.

In order to center the shaft 28 within the sleeve 26 and to facilitate its sliding action within the sleeve 26, a linear bushing 62 is located within a second annual recess 64 in the connector 42.

The jaw 30 comprises an angular extension of the distal end of the sleeve 26. The angular extension is slightly thicker than the thickness of the sleeve's sidewall and includes an inner surface 66 having a plurality of transversely extending serrations to form a good tissue grabbing surface. The jaw 32 comprises an extension of the shaft 28 and also includes a serrated inner surface 66 (See also FIG. 2).

The cross sectional profile of each of the jaws taken perpendicularly to their longitudinal axis 68 is generally semicircular so that when the jaws are fully closed, i.e., when their serrated inner surfaces 66 abut, the profile of the conjoined jaws 30 and 32 is circular and of very small diameter, e.g., 0.094 inch (2.39 mm) or less, while the conjoined free distal end surfaces of the jaws form the heretofore described tapered or rounded piercing tip 20.

The piercing member 20 will now be described with reference to FIGS. 1 and 3. As can be seen therein the member 20 basically comprises an elongated needle-like member 20A of small diameter, e.g., 1/16 inch (1.6 mm) and an enlarged cap or head 20B, e.g., ¾ inch (19 mm), mounted on the top end of the member 20A. The free end of the needle-like member 20A is in the form of a very sharp point 20C, and can be in any form, e.g., a cone, chamfer, or flechete. The needle-like member 20A is formed of any suitable material, e.g., stainless steel, and extends through a passageway 100 (FIGS. 1 and 4) extending along the central longitudinal axis 68 of the conjoined jaws 30 and 32. In particular the passageway 100 is formed by conjoining longitudinally extending recesses 102 (FIG. 2) in each of the jaws 30 and 32 and by a bore 100A contiguous with the recess 102 in the jaw 32. When the jaws are conjoined their recesses 102 conjoin with each other and with the bore 100A to complete the passageway 100. When the needle-like portion 20A is in place within the passageway, the cap 20B of the piercing member 20 is disposed over the portion of the instrument from which the jaws extend.

The external diameter of the needle-like member 20A is just slightly smaller than the internal diameter of the passageway 100 so that the member 20A can be slid in either direction therethrough. Accordingly, the piercing member is arranged to be slid distally through the passageway 100 by the user of the instrument pressing on its cap 20B so that its piercing tip 20C extends slightly, e.g., 2–2.5 mm, beyond the distal free end of the conjoined jaws. It is in this position that the piercing member 20 is ready to form the nick in the skin of the patient. The cap also serves as a convenient handle to enable the user of the instrument to grasp it during the formation of the percutaneous incision or puncture to stabilize the instrument and facilitate the formation of that incision or puncture (as will be described later).

Once the nick has been formed by the member 20, the member 20 may be retracted by pulling on the cap 20B so that its pointed end 20C is retracted within the passageway 100 and is no longer exposed out the distal end of the instrument during the passage through the underlying tissue into the abdomen. Alternatively, the member 20 may be retracted after the distal end of the instrument has entered the abdomen. In either case, as will be appreciated by those skilled in the art, when the distal end of the instrument is within the patient's body and the sharp piercing tip 20C is retracted in the instrument it will not pose a hazard to internally located tissue.

The operation of the instrument 10 to effect reflection of some internally located tissue, e.g., a lobe of the liver 12, will now be described with reference to FIGS. 4–9. To accomplish that operation the skin 16 and underlying tissue 18 of the patient's abdomen and which are located over the patient's liver 12 is preferably insufflated with any suitable gas. Once this has been accomplished the surgeon grasps the instrument 10 in one hand, with his/her thumb disposed on the cap 54 at the proximal end of the instrument and with his/her forefinger and index finger of that hand disposed on the respective extending tabs 58. The surgeon then uses his/her other hand to push on the cap 20B of the piercing member 20 to move it to the extended position shown in FIGS. 1 and 4.

The instrument 10 is now ready to form the percutaneous incision or puncture 14 into the patient's abdomen. To that end, as shown in FIG. 4, the surgeon brings the tip 20C of the extended piercing tip 20 into engagement with the patient's skin 16 located over the operative internal situs, e.g., the insufflated abdomen, and uses one hand on the cap 20B and the other hand on the handle forming the proximal portion of the instrument to orient the instrument so that the conjoined angularly extending jaws are oriented in the desired direction, e.g., substantially perpendicular, with respect to the patient's body, as shown. The surgeon then pushes on the cap 20B of the piercing member 20 so that the perpendicularly extending portion of the instrument is directed inward, i.e., toward the patient's abdomen. This action causes the piercing tip 20C to pierce into and through the derma a short distance, e.g., 2–2.5 mm., to form a shallow nick 14A (FIG. 4). The piercing tip 20C may then retracted, i.e., pulled back, so that it is within the passageway 100 like shown in FIG. 5. Alternatively, the piercing tip can be left in the extended position. In any case the surgeon continues to hold the cap of the piercing means in one hand, as shown in FIG. 4, to stabilize the instrument, e.g., prevent it from twisting, as he/she pushes inward on the instrument using his/her other hand holding the proximal portion of the instrument. This action enables the tissue engagement surface at the free end of the conjoined jaws to pass through the nick 14A and into and through the underlying tissue 18 (as shown by the phantom lines in FIG. 5) until the distal end of the conjoin jaws passes completely through the underlying tissue 18 (shown in progress in FIG. 6) to enter into the abdomen, as shown in FIG. 7, whereupon a small percutaneous incision or puncture 14 is formed and completed.

If the piercing tip 20C had not been retracted into the passageway 100 yet it is retracted at this time so that it is no longer exposed. In fact once the free end of the jaws has entered into the abdomen the piercing member is completely removed from the instrument (as shown in FIGS. 7–9) to enable the working head, e.g., the complete jaws, to be located within the abdomen to perform the tissue reflection procedure.

Thus, once the conjoined angularly extending jaws are fully within the insufflated abdomen the instrument 10 is then oriented as shown in FIG. 8 so the contiguous longitudinally extending portion of the sleeve assembly 24 passes into the percutaneous incision or puncture 14. Continued inward pushing on the instrument forces more of the sleeve assembly through the puncture 14 until the conjoined jaws 30 and 32 are at the desired internal position. This procedure can be monitored visually or electronically via any conventional means, e.g., a laparoscope.

Once the jaws 30 and 32 are free of the percutaneous incision or puncture, i.e., are within the abdomen, and adjacent the tissue to be reflected, they may be opened to grasp that tissue therebetween. To accomplish that result the surgeon applies thumb and finger pressure to the thumb cap 44 and finger tabs 58, respectively, to move the plunger element 50 further into the housing. The movement of the plunger causes the concomitant movement of the shaft 28 within the sleeve 26 against the bias force produced by the compression spring 60. This action has the effect of moving the jaw 32 away from the jaw 30, thereby opening the jaws, like shown by the phantom lines in FIG. 5, whereupon the instrument can be manipulated so that a portion of the desired lobe of the liver be located between the open jaws.

In order to grasp that tissue the surgeon merely has to release the thumb pressure on the cap, whereupon the spring 60 carries the plunger element and the shaft 28 in the proximal direction until the jaws 30 and 32 close on the interposed tissue 12. That tissue can then be held in position or reflected, as shown in FIG. 9, depending upon the desires of the surgeon.

Once the laparoscopic procedure has been accomplished, the surgeon may release the grasped tissue by again applying thumb pressure on the thumb cap 54 while his/her fingers hold the tabs 58. After the tissue is released the instrument 10 can be readily slid out of the percutaneous incision or puncture 14, so that the incision or puncture immediately closes and seals itself.

The passageway 100 in the conjoined jaws serves as convenient means for enabling a conventional guide wire 300 to be extended therethrough. By so doing ready access to the interior of the patient's body through the same percutaneous incision or puncture 14 may be provided. For example, after the instrument 10 has performed its desired function, a guide wire 300 can be inserted (as will be described hereinafter), and the original instrument 10 removed, leaving the guide wire 300 in place extending through the percutaneous incision or puncture 14. Thus, if desired, another instrument 10 or a different type of instrument (not shown) can be inserted on the guide wire 300 and slid through the percutaneous incision or puncture. This action is shown in FIGS. 10–12. In particular, if it is desired to place a guide wire 300 into the patient's insufflated abdomen through the incision or puncture 14, this action is accomplished by moving the instrument 10 to the orientation shown in FIG. 10, whereupon the hole 100A of the passageway 100 is located outside of the patient's body, while the opposite end of the passageway 100 is within the insufflated abdomen. The distal end of the guide wire 300 can then be slid into the opening 100A and down through the passageway 100 until it is within the insufflated abdomen, as shown in FIG. 10. The instrument 10 can then be retracted out of the percutaneous incision or puncture 14, leaving the guide wire 300 in place therein, whereupon the percutaneous incision or puncture closes about the guide wire, as shown in FIG. 11. With the guide wire 300 in place, another instrument having a guide wire passageway in its distal end can be threaded on the proximal portion of the guide wire 300 and slid down the guide wire so that it enters and passes through the percutaneous incision or puncture. This action is shown in FIG. 12. The guide wire thus can be used to facilitate and guide the introduction of the instrument into the insufflated abdomen.

Once the laparoscopic procedure has been accomplished the instrument can be readily removed from within the insufflated abdomen by sliding it out along the guide wire (assuming that it had been left on the guide wire or else had been placed on the guide wire within the insufflated abdomen). Then the guide wire 300 can be retracted out of the percutaneous incision or puncture, whereupon the incision or puncture closes and seals itself in the same manner as described earlier. As should be appreciated by those skilled in the art, if desired, the instrument and the guide wire can be removed together from the percutaneous incision or puncture if the instrument is still on the guide wire. It is, of course contemplated that the guide wire can be removed from the instrument while the instrument is in place within the patient's body. In such a case, after the guide wire is removed and the instrument has accomplished its desired procedure it can be removed from the patient's body in the same manner as described earlier.

Referring now to FIGS. 13–15 the details of an alternative piercing member or device 200 for use with the instrument 10 will now be described. As can be seen therein the device 200 basically comprises an elongated somewhat tubular member 202 having a linear central passageway 204 whose inside diameter is just slightly larger than the outside diameter of the conjoined jaws 30 and 32 so that those conjoined jaws can extend through the passageway 204. In the embodiment shown herein the tubular member 202 is not a closed circular tube, but rather is a thin sheet of any suitable material, e.g., stainless steel, bent into a circular arc of approximately 270 degrees, e.g., the outside diameter of which is 0.109 inch (2.77 mm), so that its free edges define a longitudinally extending slot 206. An enlarged cap or head 208, e.g., ¾ inch (19 mm), is mounted on the top end of the tubular member 202 and the cap includes a recess 210 in its undersurface to receive a portion of the conjoined jaws 30 and 32. The free end of the tubular member 202 is cut at an angle to form a very sharp point 212.

The piercing device 200 is arranged to be slid over the conjoined jaws 30 and 32, i.e., the conjoined jaws being located within the central passageway 204 of the member 200, so that its piercing point 212 extends slightly, e.g., 2–2.5 mm, beyond the free end of the conjoined jaws, as shown in FIG. 13. It is in this position that the piercing member 200 is ready to form the nick in the skin of the patient, in a similar manner as described earlier. This action is shown in FIGS. 16 and 17.

The cap 208, like the cap 20B, serves as a convenient handle to enable the user of the instrument 10 to grasp it during the formation of the percutaneous incision or puncture to stabilize the instrument and facilitate the formation of that incision or puncture, in the same manner as described earlier.

Once the nick in the skin of the patient has been formed by the member 200, the member 200 may be removed or merely retracted by pulling on the cap 208 in a direction away from the free end of the conjoined jaws 30 and 32. Once the member has been removed or retracted, The instrument 10 can then be used to penetrate the underlying tissue to form the percutaneous incision or puncture 14 in the same manner as described earlier. Alternatively, the piercing device 200 may be removed or retracted after the distal end of the instrument 10 has entered the abdomen. In either case, as will be appreciated by those skilled in the art, the piercing device 200 must be removed from the conjoined jaws 30 and 32 to free them so that they can be opened before the instrument can be used to grasp internally located tissue. The removal of the piercing device 200 from the instrument 10 not only frees the jaws, but also eliminates any potential danger of injury to internally located tissue which could occur if the piercing tip 212 was within the insufflated abdomen.

The operation of the instrument 10 to effect reflection of some internally located tissue, e.g., a lobe of the liver 12, after the piercing device 200 has been removed is accomplished in the same way as that described earlier, and is shown in the illustrations of FIGS. 19–21.

In FIGS. 22–28 there are shown further alternative embodiments of a piercing device constructed in accordance with this invention for carrying out the methods of this invention. Those embodiments are designated by the reference numerals 400, 500, and 700. Each of these devices is arranged to be used on an instrument in a somewhat similar manner to that described with reference to the device 200. For example the devices 500 and 700 are configured to be used in a similar manner to that described heretofore on the instrument 10 or any other instrument 800 (FIG. 26) having an angularly extending working head. The device 300 is configured to be used in a similar manner on an alternative instrument 600, which includes a linearly extending distal working head.

The details of each of the devices 400, 500, and 700, and of the instruments 600 and 800 will be described later. Suffice it for now to state that each of the devices 400, 500, and 700 includes a piercing tip and is arranged to be disposed on the distal end of an instrument so that the piercing tip extends beyond the free end of the working head of the instrument. The instrument with the piercing device thereon is than brought into engagement with the skin and pushed inward so that the device forms a puncture or nick of a predetermined depth through the skin and underlying tissue (in the case of abdominal surgery the depth of the nick is preferably through the skin and a portion of the subcutaneous fat, but not through the peritoneum). The device is then retracted, e.g., removed from the nick, and then the instrument is pushed inward so that the distal end of the instrument passes through the nick and through the tissue underlying that nick (e.g., the remainder of the subcutaneous fat and the peritoneum) to form or complete a percutaneous incision or puncture and to locate its working head within a desired interior portion of the being's body (e.g., the abdomen) without necessitating the use of a trocar or other introducing instrument.

Once the working head of the instrument is in place, as just described, it may be operated from outside the patient's body to perform its desired function, e.g., clamping and reflecting a lobe of the liver 12 in a manner like that described earlier. At this time the tissue contiguous with the incision or puncture engages the instrument sufficiently tightly to form a fluid tight seal, e.g., a seal sufficient to preclude the egress of any insufflation gas from the interior of the patient's body.

After the procedure has been completed the instrument is retracted out of the incision or puncture whereupon it closes and seals itself. In this regard, in accordance with a preferred aspect of this invention the piercing device and the instrument on which it is used is of a very small diameter, like that described heretofore, so that when the instrument is removed from the percutaneous incision or puncture the incision or puncture seals itself almost immediately, and only a very small scar, if any, results upon healing.

Referring now to FIGS. 22–24 the details of the piercing device 300 and the instrument 600 will now be discussed. In particular, the instrument 600 is of somewhat conventional construction and basically comprises an elongated body portion 602 having a proximal end at which a pair of handles 604 and 606 are located, and a distal end at which a working head 608 is located. The handle 604 is fixed, and the handle 606 is pivotable. The working head comprising a pair of jaws, one of which 610 being fixed, and the other 612 being pivotable. The jaws are oriented so that when they are closed, i.e., abutting and conjoining, they extend in a direction parallel to the longitudinal axis of the elongated body portion. In particular, the surfaces of jaws which abut each other when the jaws are closed are collinear with that longitudinal axis. It must be pointed out at this juncture that the use of the term "axis" in this application is in the broadest possible sense and context, and, hence, is not limited to a straight line, but can be a line of any shape, e.g., a curved line, since the body portion 602 need not be straight.

The body 602 comprises an elongated sleeve 614 whose proximal end is connected to the handle 604. In particular, the handle 604 comprises an elongated shank 616 having a finger hole 618 at its lower end and a tubular coupling or joint 620 at its upper end. The proximal end of the elongated sleeve 614 is located and fixedly secured within the tubular joint 620.

The fixed jaw 610 of the working head is located at the distal end of the sleeve 614. In fact, in the jaw 610 may be formed integrally with the sleeve 614. The pivoting jaw 612 of the working head includes a rear projection 622 in which a pivot pin 624 is located. The pivot pin 624 is mounted within the sleeve 614 at its merger point with the jaw 610 to pivotably connect the jaw 612 to the jaw 610. The free end of the projection extends through a hole 626 in the sleeve 614. In order to pivot the jaw 612 with respect to jaw 610 an elongated push rod 628 is provided extending through the sleeve 214. The distal end of the rod 628 is connected to the jaw 612 via a pivot pin 630. The proximal end of the rod 628 is pivotably connected to the handle 606 via a pivot pin 632. In particular, the handle 606 includes an elongated shank 634 having a finger hole 636 at its lower end and a pair of holes 638 and 640 at its upper end. The hole 638 receives the pivot pin 632 to pivotably connect the handle 606 to the rod 628.

The pivoting handle 606 is pivotably connected to the fixed handle 604 via a pivot pin 642 which extends through the other hole 640 in the upper end of the handle 606. The pivot pin 642 is, in turn, mounted between a pair of aligned holes in a pair of spaced projections or brackets 644 extending to the rear of the tubular joint 620.

The pivoting jaw 612 is arranged to be pivoted away from fixed jaw 610 by spreading the user of the instrument spreading the handles 604 and 606 apart by his/her fingers in the finger holes 618 and 636, respectively, whereupon tissue can be located in the mouth between the open jaws. The jaws can then be used to grasp that tissue by squeezing the handles together, thereby causing the jaw 610 to pivot toward the jaw 612. In order to facilitate the grasping of tissue each of the jaws includes plural serrations 646 on its tissue engagement surface.

When the jaws 610 and 612 are completely closed, such as shown by the full lines in FIG. 24, they abut each other, whereupon the outer periphery of the conjoined jaws is substantially circular and of the very small cross sectional area, like that discussed earlier. Moreover, the distal end of each jaw is somewhat rounded, and when the jaws are conjoined they form the heretofore identified tissue engagement surface. It is in the conjoined jaw configuration that the instrument 600 is used to pierce through the nick formed in patient's skin and underlying tissue. That nick is formed by the piercing device 400.

The piercing device 400 basically comprises an elongated somewhat tubular member 402, which is constructed similarly to tubular member 202 of the device 200 described earlier. Thus, the member 402 has a linear central passageway 404 whose inside diameter is just slightly larger than the outside diameter of the conjoined jaws 610 and 612 so that those conjoined jaws can extend through the passageway 404, The tubular member 402 is not a closed circular tube, but rather is a thin sheet of any suitable material, e.g., stainless steel, bent into a circular arc of greater than 180 degrees so that its free edges define a longitudinally extending slot 406. An enlarged cap or head 408 is mounted on the top end of the tubular member 402 and the cap includes a recess 410 in its undersurface to receive a portion of the conjoined jaws 610 and 612. The free end of the tubular member 402 is cut at an angle to form a very sharp point 412.

A handle 414 is mounted on the cap 408. The handle basically comprises a pair of looped members defining finger holes 416 and 418. The looped member defining the finger hole 416 is split into two sections 416A and 416B so as to create a space or slot 420 (FIG. 23) between the split sections. The slot 420 is aligned with the slot 406 in the tubular member 402 in order to enable the conjoined jaws 610 and 612 of the instrument 600 to be passed laterally through the slot 420 and through the slot 406 to snap fit with the interior of the passageway 404 in the tubular member 402.

The device 400 is slidable with respect to the conjoined jaws so at its pointed end 412 extends slightly, e.g., 2–2.5 mm, beyond the rounded free ends of the conjoined jaws 610 and 612. It is in this position that the piercing member 400 is ready to form the nick in the skin and some underlying tissue of the patient to start the formation of the percutaneous incision or puncture. In order to hold the device 400 in the desired extended position its tubular member 402 includes a small dimple or detent 422 arranged to engage the instrument 600 at the point at which the pivoting jaw 612 is connected to the push rod.

In accordance with a preferred embodiment of this invention the device 400 is arranged to pierce the skin and underlying tissue to form a nick of a predetermined depth. For example, for applications wherein access to the abdomen is desired, the device 400 is arranged to produce a nick whose depth extends through the skin 16, and through a portion of the underlying subcutaneous fat and fat 18, but not through the peritoneum 19. This automatic depth penetration control is accomplished by the inner surface of the cap making contact with the surface of the skin. To that end the length of the tubular member 402 is selected so that its pointed end 412 will reach the maximum depth desired for the nick at the time that the inner surface 408A of the cap makes contact with the patient's skin.

The finger holes 416 and 418 of the handle enable the user of the instrument 400 to grasp it during the formation of the percutaneous incision or puncture to stabilize the instrument and facilitate the formation of that incision or puncture, in the same manner as described earlier.

Once the nick in the skin and underlying tissue has been formed to the appropriate depth by the member 400, the member 400 may be removed or merely retracted by pulling on the finger holes of the cap in a direction away from the free end of the conjoined jaws 610 and 612. Once the member has been removed or retracted. The instrument 600 can then be used to penetrate the tissue, e.g., the peritoneum, underlying the nick to form, i.e., complete, the percutaneous incision or puncture 14 in the same manner as described earlier. This action locates the working head at the desired internal position, whereupon it can be operated to open its jaws to grasp and reflect tissue, e.g, to reflect the lobe of the liver as described earlier.

Like before, the removal of the piercing member 400 from the instrument 600 not only frees the jaws, but also eliminates any potential danger of injury to internally located tissue which could occur if the piercing tip 412 was within the insufflated abdomen since the surfaces of the jaws are sufficiently blunt to pose no hazard to internally located tissue, e.g., tissue within the insufflated abdomen.

In FIG. 25 there is shown an alternative embodiment 500 of the piercing device. That device is similar in construction to the device 400, except that its cap includes a single finger ring. Moreover, the device 500 is used in the same manner as described with reference to the device 400. Thus, in the interests of brevity the components of the device 500 which are the same as those of device 400 are given the same reference numbers and their description will not be reiterated.

The cap 402 of the device 500 has a finger ring 502 projecting upward therefrom. The finger ring 502 includes a slot 504 in it. This slot is similar to the slot 410 described heretofore, except that it is angled so that the device 500 can be used on an angled working head instrument, like the instrument 10 or the instrument 800 shown in FIG. 26. The instrument 800 is identical in construction to the instrument 600 except that its working head jaws 610' and 612' extend at an acute angle to the longitudinal axis of the body of the instrument. In the interest of brevity the details of the construction and operation of the instrument 800 will not be reiterated.

In FIG. 25A there is shown a plan view of the nick or puncture formed by the devices 400 and 500. Thus, as can be seen the portion of the puncture or nick, formed by the piercing tip is shown by the solid line designated by the reference letter "N", and is of arcuate shape and extends for a substantial portion, e.g., approximately 180 degrees. The remainder of the puncture or nick is shown by the phantom lines, and designated by the reference letter "I", represents the boundary of the percutaneous incision or puncture formed by the instrument passing through the nick to open it further, dilate it. In order to minimize the size of the puncture or nick formed by the piercing device of this invention, the piercing tip may be formed like that shown in the embodiment of the device 700 of FIG. 27. That embodiment is identical in all respects to the embodiment 500 except that the piercing tip comprises a sharp leading cutting edge 712A for piercing tissue, i.e., forming the nick or puncture, and a trailing blunt spreading edge 712B disposed proximally of said leading cutting edge for spreading the tissue cut by said leading cutting edge. FIG. 27A is a plan view similar to that of FIG. 25A, but showing the puncture or incision "N" formed by the device 700. As can be seen therein the incision is of smaller size and will thus leave less of a scar.

It should be pointed out at this juncture that the piercing devices 200, 300, 400, 500, and 700 may be used in a different manner than that described heretofore to form a percutaneous incision or puncture and serve as a portal through which an instrument can be extended. In this regard the devices 200, 300, 400, 500, and 700 may be used in a manner similar to the use of yet another alternative embodiment 900 of a piercing device of this invention. The piercing device 900 is shown in FIG. 29 and constitutes the most preferred embodiment of this invention.

The details of the construction and most preferred use of the device 900 will be described shortly. Suffice it for now to state that the device 900 (as well as the other piercing devices 200, 300, 400, 500, and 700) is preferably used by itself, i.e., it is not mounted on an instrument, to pierce through the skin and underlying tissue to form a trough shaped percutaneous incision or puncture to the insufflated abdomen or any other internal portion of the being's body. The piercing device 900 is arranged is left in place within the trough shaped percutaneous puncture so that it forms a portal through which any suitable instrument can later be extended and guided. As will be described later the tissue contiguous with the portion of the piercing member which extends through the trough shaped puncture intimately engages the surfaces of that portion to form a substantially fluid-tight interface therewith. This action effectively prevents the insufflating gas from escaping from the abdomen. Once the piercing member has formed the trough shaped percutaneous puncture the instrument can be inserted through the puncture, while being guided by surface portions of the piercing member, until the working head of the instrument is located at the desired position, e.g., within the insufflated abdomen. Once the instrument is in place the piercing device can be removed, e.g., slid proximally off of the instrument, leaving the instrument in place extending through the percutaneous puncture. The tissue contiguous with the puncture also forms a substantially fluid-tight interface with the external surface of the portion of the instrument extending therethrough to prevent the insufflating gas from escaping from the abdomen. The instrument can then be operated to enable its working head to perform the desired procedure within the insufflated abdomen, e.g., grasping and reflecting a lobe of the liver.

It should be pointed out at this juncture that the piercing device 900 (as well as the devices 200, 300, 400, 500, and 700) can be used with any type of instrument, not merely those described heretofore, so long as the instrument is of suitable cross sectional area to be extended through the device, as will be described later.

Referring now to FIG. 29 the details of the piercing device 900 will now be described. As can be seen the device 900 basically comprises an elongated guide member 902 and a head or handle 904. The guide member 902 comprises an elongated trough shaped sidewall has an inner surface 906 and an outer surface 908 (FIG. 30). The inner surface is of semicircular shape when viewed perpendicularly to the longitudinal axis of the member 902 and defines a trough shaped recess. The outer surface 908 is also of semicircular shape when viewed perpendicularly to the longitudinal axis. The guide member is formed of any suitable material, e.g., stainless steel. In one exemplary embodiment the guide member is formed of a sheet of stainless steel whose thickness is 0.015 inch (0.38 mm), with the outer diameter of the outside surface 908 of the guide member being 0.25 inch (6.35 mm) and its length 2.5 inches (63.5 mm).

A pair of offset tabs or ears 910 (FIGS. 30 and 31) are provided adjacent the proximal end of the elongated guide member 902. The tabs 910 project outward diametrically from each other perpendicularly to the longitudinal axis of the guide member. These tabs serve as the means for securing the guide member 902 to the cap 904.

The cap 904 basically comprises a generally H-shaped member, when viewed in cross section (such as in FIG. 30), and is formed of any suitable material, e.g., is molded of high density polyethylene. The cap 904 includes a lower flange having a planar bottom surface 914 (FIG. 31) extending perpendicularly to the longitudinal axis of the guide member. The surface 914 of the flange serves as a stop surface, like that described heretofore.

A slot 916 extends from one edge of the flange 912 to the center of the cap 904. The inner end 918 of the slot 916 is of semicircular shape to accommodate the proximal end of the guide member 902 therein and to provide a trough shaped passageway 920 collinear with the trough shaped recess 906. A pair of opposed locking slots 922 extend perpendicularly from the slot 916 immediately adjacent the passageway 920 to receive respective ones of the tabs 910. The width of each locking slot 922 is slightly less than the amount of offset of the tab 910 located therein so that the tab is tightly held within the slot 922, thereby fixedly securing the cap to the guide member. Plural nibs 924 project inward from the cap contiguous with the locking slots 922 to serve as a seat upon which the locking tabs 910 rest. Additional securement means (not shown) may be used to further enhance the securement of the cap to the guide member.

As can be seen clearly in FIG. 31 the distal end portion of the guide member tapers slightly inward at 926, i.e., is slightly conical, and terminates in a sharpened piercing tip 928.

Figure 36:
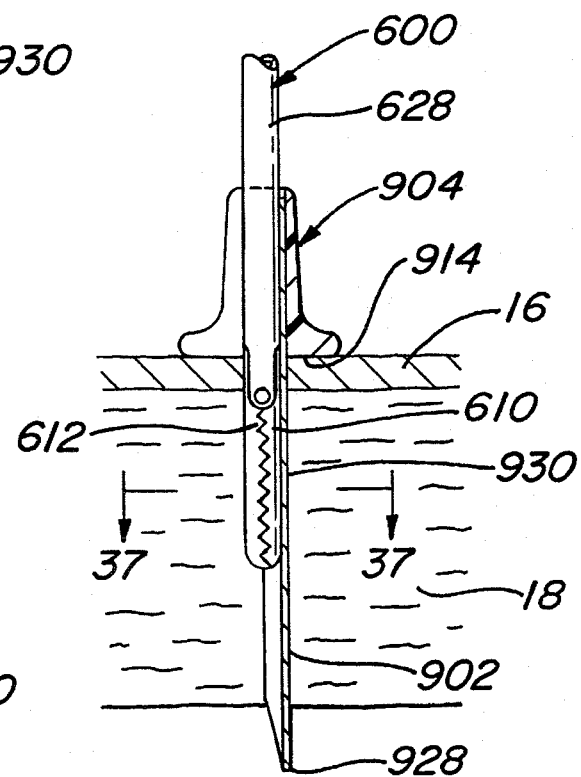
FIG. 36 is an illustration, like that of FIG. 33, but showing the piercing device of FIG. 29 during the process of guiding an instrument through the trough shaped percutaneous puncture into the insufflated abdomen.
Figure 38:
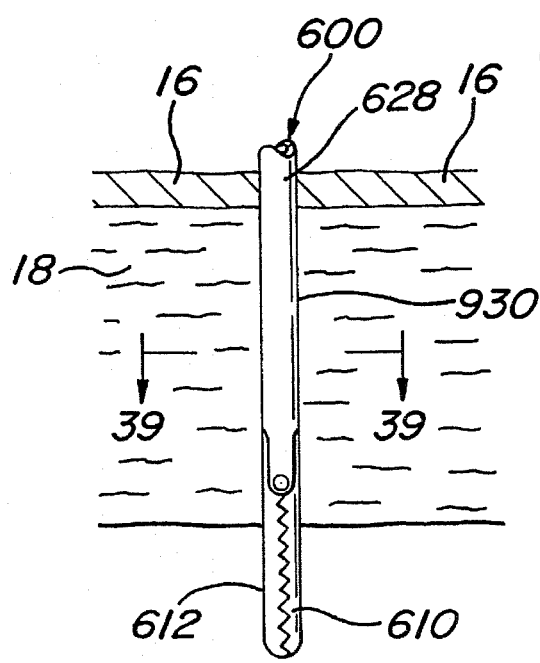
FIG. 38 is an illustration, like that of FIGS. 33 and 36, but showing the instrument extending through the percutaneous puncture after the piercing device of FIG. 29 has been removed therefrom.

Operation of the piercing device 900 will best be understood by reference to FIGS. 33, 36, and 38. The intended puncture site, e.g., the insufflated abdomen, is visualized intra-abdominally by any suitable means, e.g., a laparoscope (not shown). The site is then palpated to verify adequate insufflation pressure and working space. The piercing device 900 is then grasped by its cap 904 and brought to the puncture site so that its longitudinal axis is generally perpendicular to the surface of the skin at the site. An axial force is then applied to the cap in the distal direction so that the piercing tip 928 engages the surface of the skin at the puncture site. This causes the piercing tip to readily pierce through the skin. Continued force enables the tip to pass through the underlying tissue until the cap's stop surface 914 engages the surface of the skin as shown in FIG. 33. The distance between the piercing tip and the stop surface is selected so that when the stop surface engages the skin the piercing tip will have just entered the insufflated abdomen, but will not project too far in where it could injure some organ or tissue therein.

Since the guide member 902 is trough shaped, the percutaneous puncture 930 produced by its passage through the skin and underlying tissue is correspondingly trough shaped, as shown in FIG. 35. Moreover, and quite significantly, as shown clearly in FIG. 35 the tissue 932 contiguous with the puncture intimately engages the inner and outer surfaces 906 and 908, respectively, of the guide member to form a substantially fluid-tight interface therebetween. This action ensures than the insufflation gas does not leak out of the puncture.

Once the piercing member is in the position like that shown in FIG. 33 it serves as a portal for enabling an instrument, e.g., instrument 600, to be extended and guided therethrough. To accomplish that end the shank 628 of the instrument is aligned with the longitudinal axis of the piercing device. With the instrument in this orientation its distal end, e.g., the conjoined working jaws 610 and 612 are extended through the passageway 920 and into the axially aligned trough shaped recess 906. The instrument is then slid in the distal direction, with the inner surface 906 of the guide member guiding the passage of the instrument through the percutaneous puncture like shown in FIG. 36. The instrument is extended through the puncture until its working head jaws are free within the interior of the insufflated abdomen. During the insertion of the instrument through the puncture as guided by the guide member the tissue 932 contiguous with the puncture intimately engages the outer surface of the guide member and the contiguous outer surface of the instrument as shown in FIG. 37, thereby creating a substantially fluid-tight interface therebetween to prevent loss of insufflation.

When the working head of the instrument is at the desired position within the insufflated abdomen the instrument 600 the piercing member is removed from the puncture. This is accomplished by holding the instrument in place and grasping the cap 904 of the piercing instrument and pulling on it in the proximal direction. This action causes the piercing member to slide along the instrument's shank 628 until the piercing tip 928 clears the surface of the skin. The piercing device can then be removed from the instrument via its slot 916. This action leaves the instrument extending through the percutaneous puncture as shown in FIG. 38. The tissue contiguous with the puncture intimately engages the outer surface of the instrument extending therethrough in a substantially fluid-tight interface as shown in FIG. 39 so that insufflation is maintained. The instrument can now be operated so that its working means, e.g., jaws, perform the desired function within the insufflated abdomen.

When the instrument has completed its desired procedure it may be removed by pulling it in the proximal direction while directly visualizing the removal intra-abdominally. The trough shaped puncture should then be inspected for hemostasis.

Figure 40:
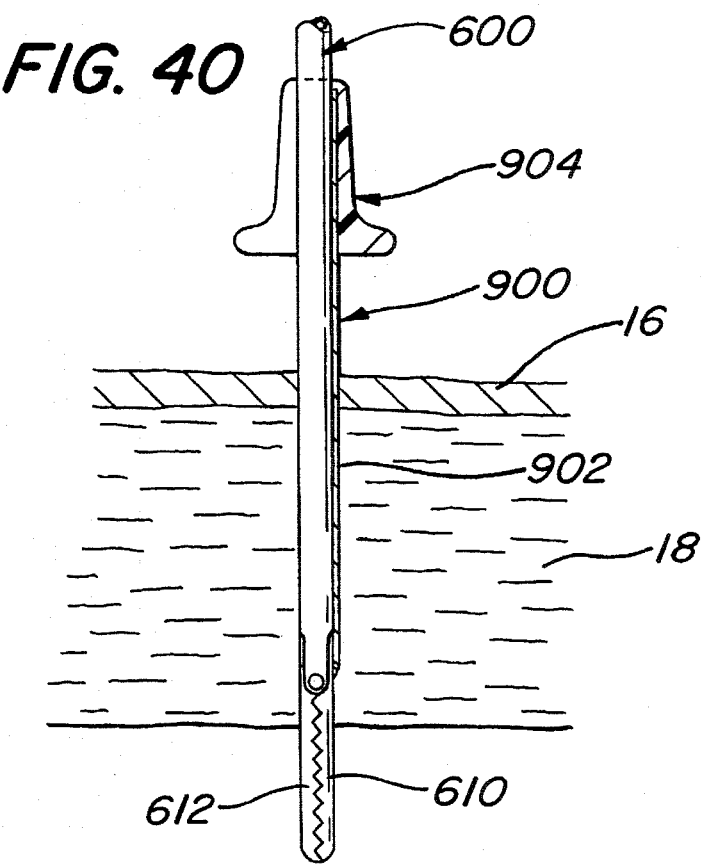
FIG. 40 is an illustration, like that of FIGS. 33, 36 and 38, but showing a piercing device in the process of being slid down and instrument extending through a percutaneous puncture after the instrument has completed its procedure to enable the instrument to be removed from the percutaneous puncture to leave the piercing device in the percutaneous puncture to serve as a portal for access by the same or another instrument.

As should be appreciated by those skilled in the art with the subject invention the exchange of instruments can be readily accomplished via the same percutaneous incision or puncture. To that end with the original instrument still in place, like shown in FIG. 38, the piercing device 900 can be slid onto the shank of the instrument via its slot 916 and when in place the piercing device can then be slid in the distal direction down the instrument taking care to align the trough shaped guide member with the original puncture until the stop surface 914 engages the skin. This action is shown in FIG. 40. The instrument can then be removed in the same manner as described heretofore leaving the piercing member 900 in place to form a portal. A new instrument can then be inserted through the portal in the same manner as described heretofore. As should be appreciated that once a puncture has been formed by a piercing device 900 the exchange of an instrument can be achieved with a alternative piercing device, i.e., one whose distal end is not sharp.

Figure 41:
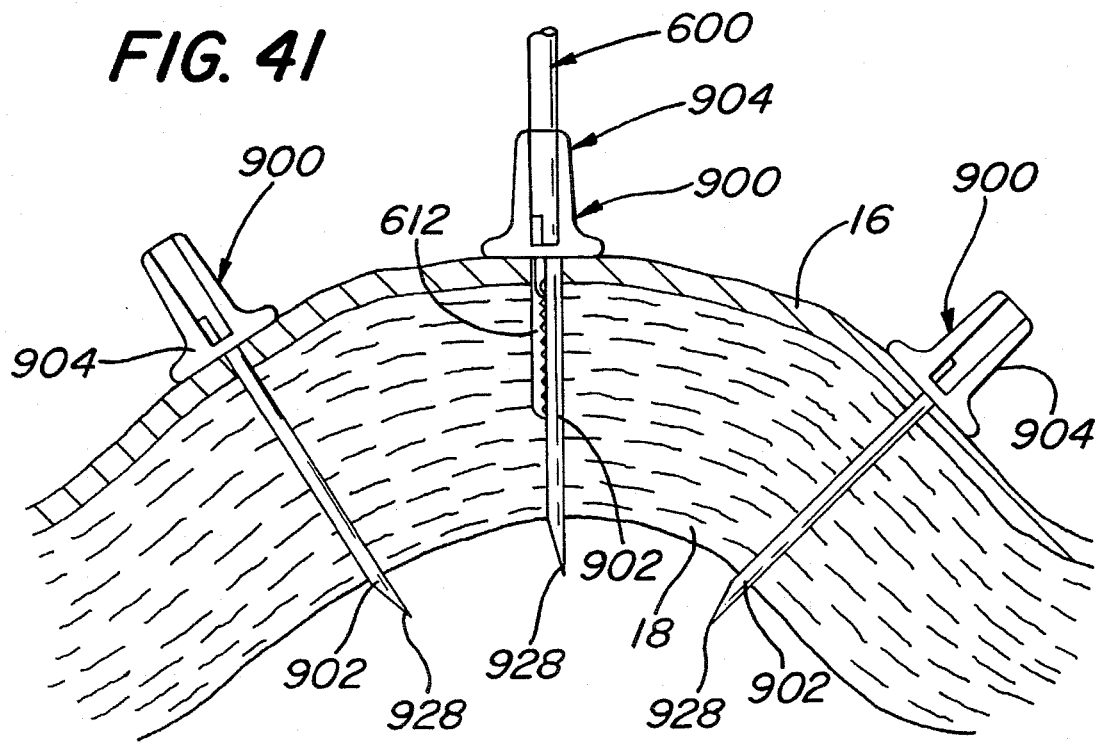
FIG. 41 is a cross sectional illustration of an insufflated abdomen showing several piercing devices of the subject invention in place forming plural portals for access to the interior of the insufflated abdomen by one or more instruments.

As should also be appreciated by those skilled in the art plural piercing devices can be used to provide plural portals to an insufflated abdomen for insertion of various instruments therethrough as illustrated in FIG. 41.

Without further elaboration, the foregoing will so fully illustrate my invention that others may, by applying current or future knowledge, readily adopt the same for use under various conditions of service.

What is claimed is:

1. A piercing device for use by a person performing minimally invasive surgery, the surgery being performed by extending a medical instrument through the skin and underlying tissue to an internal portion within the body of a living being, the instrument having a proximal portion and a distally located working portion arranged for performing some medical procedure in the internal portion of the body of the being, said piercing device comprising:

(A) a guide member comprising an elongated trough shaped sidewall having:
 (1) an inner surface defining a trough shaped recess,
 (2) an outer surface,
 (3) a distal end portion, and
 (4) a proximal portion,
 said distal end portion comprising a piercing tip, said trough shaped recess having a pair of marginal edges, (B) a head portion being located at said proximal portion of said guide member and being shaped to enable said head portion to be readily held by the person, said piercing tip in engagement with the skin of the being, said proximal portion of said guide member being located outside of the body of the being over the internal portion of the being's body and extended through the skin and at least a portion of the underlying tissue, wherein said elongated trough shaped sidewall forms a trough shaped percutaneous puncture which extends to the surface of the skin, said trough shaped sidewall being configured so that the tissue contiguous with the puncture engages both of said inner and outer surfaces of said sidewall to form a substantially fluid-tight interface therewith, said inner surface of said guide member being shaped to slidably receive said working portion of the instrument thereon, wherein said working portion can be readily slid therealong and guided thereby after said device has formed the puncture so that said working portion passes through the puncture into the internal portion, said marginal edges of said guide member being spaced apart sufficiently to enable said piercing device to be readily removed from the puncture and the instrument to leave the instrument in place within the puncture by passing the working portion of the instrument between said marginal edges of said guide member without deforming the working portion so that the instrument can be operated by the person to perform the medical procedure within the internal portion of the body of the being.

2. The piercing device of claim 1 wherein said head portion comprises a handle including an opening communicating with said trough shaped recess in said guide member to provide a passageway through which the working portion of the instrument can be extended.

3. The piercing device of claim 1 wherein said trough shaped recess is linear.

4. The piercing device of claim 1 wherein said head portion comprises a skin engaging stop surface, and wherein said piercing tip is a predetermined distance from said stop surface so that said tip can not be extended excessively deeply into the body of said being.

5. The piercing device of claim 4 wherein said skin engaging stop surface comprises a flange.

6. The piercing device of claim 4 wherein said predetermined distance is at least 10 mm.

7. The piercing device of claim 1 wherein at least one of said inner surface and said outer surface are arcuate in cross section.

8. The piercing device of claim 1 wherein said trough shaped recess of said guide member is open along the length thereof to enable said device to be removed from the instrument by sliding said device longitudinally in a proximal direction until said device is outside of the puncture and thereafter sliding said device laterally off of the instrument, whereupon the working portion of the instrument passes between said marginal edges of said guide member without deforming the working portion.

9. In combination a piercing device and a medical instrument for use by a person performing minimally invasive surgery on a living being, the surgery being performed by extending said instrument through the being's skin and underlying tissue to an internal portion within the body of the being, (A) said instrument comprising:
 (1) a proximal portion arranged to be located outside the body of the being, and
 (2) a distally located working portion coupled to said proximal portion to be operated thereby to be moved relative to said proximal portion for performing some medical procedure in the internal portion of the body of the being;

(B) said piercing device comprising:
 (1) a guide member comprising an elongated trough shaped sidewall having:
  (a) an inner surface defining a trough shaped recess,
  (b) an outer surface,
  (c) a distal end portion, and
  (d) a proximal portion,
  said distal end portion comprising a piercing tip, said trough shaped recess having a pair of marginal edges,
 (2) a head portion being located at said proximal portion of said guide member and being shaped to enable said head portion to be readily held by the person,
 said piercing tip in engagement with the skin of the being over the internal portion of the being's body and extended through the skin and at least a portion of the underlying tissue to form a trough shaped percutaneous puncture extending to the surface of the skin, said trough shaped sidewall being configured so that the tissue contiguous with the puncture engages both of said inner and outer surfaces of said sidewall to form a substantially fluid-tight interface therewith, said inner surface of said guide member being shaped to slidably receive said working portion of said instrument thereon to enable said working portion to be readily slid therealong and guided thereby after said device has formed the puncture so that said working portion passes through the puncture into the internal portion, said marginal edges of said guide member being spaced apart sufficiently to enable said piercing device to be readily removed from the puncture while leaving said instrument in place by passing the working portion of the instrument between said marginal edges of said guide member without deforming the working portion so that said instrument can be operated by the person to perform the medical procedure within the internal portion of the body of the being.

10. The combination of claim 9 wherein said working portion of said instrument is substantially rigid.

11. The combination of claim 10 wherein said head portion of said device comprises a handle including an opening communicating with said trough shaped recess in said guide member to provide a passageway through which said working portion of said instrument can be extended.

12. The combination of claim 10 wherein at least one of said inner surface and said outer surface of said guide member are arcuate in cross section.

13. The combination of claim 10 wherein said trough shaped recess of said guide member is open along the length thereof to enable said device to be removed from said instrument by sliding said device longitudinally in a proximal direction until said device is outside of the puncture and thereafter sliding said device laterally off of said instrument, whereupon the working portion of said instrument passes between said marginal edges of said guide member without deforming said working portion.

14. The combination of claim 9 wherein said head portion of said device comprises a handle including an opening communicating with said trough shaped recess in said guide member to provide a passageway through which said working portion of said instrument can be extended.

15. The combination of claim 9 wherein said trough shaped recess of said device is linear.

16. The combination of claim 9 wherein said head portion of said device comprises a skin engaging stop surface, and wherein said piercing tip is a predetermined distance from said stop surface so that said tip can not be extended excessively deeply into the body of said being.

17. The combination of claim 16 wherein said skin engaging stop surface comprises a flange.

18. The combination of claim 16 wherein said predetermined distance is at least 10 mm.

19. The combination of claim 9 wherein at least one of said inner surface and said outer surface of said guide member are arcuate in cross section.

20. The combination of claim 9 wherein said trough shaped recess of said guide member is open along the length thereof to enable said device to be removed from said instrument by sliding said device longitudinally in a proximal direction until said device is outside of the puncture and thereafter sliding said device laterally off of said instrument, whereupon the working portion of said instrument passes between said marginal edges of said guide member without deforming said working portion.

21. The combination of claim 10 wherein said trough shaped recess of said device is linear.

22. The combination of claim 10 wherein said head portion of said device comprises a skin engaging stop surface, and wherein said piercing tip is a predetermined distance from said stop surface so that said tip can not be extended excessively deeply into the body of said being.

23. The combination of claim 22 wherein said skin engaging stop surface comprises a flange.

24. The combination of claim 22 wherein said predetermined distance is at least 10 mm.

25. A method for performing minimally invasive percutaneous surgery by extending a medical instrument through the skin and underlying tissue to an internal portion within in the body of a living being, said method comprising:

(a) providing an instrument having a proximal portion and a distal portion including working means, (b) providing a piercing device comprising an elongated guide member and a head portion, said guide member having a longitudinal axis and comprising an elongated trough shaped sidewall having a pair of marginal edges, an inner surface, an outer surface, a proximal portion at which said head portion is located, and a distal end portion having a piercing tip;

(c) bringing said piercing tip into engagement with the skin and pushing on said head portion to extend said guide member through the skin and underlying tissue to form a trough shaped percutaneous puncture to the internal portion, whereupon the tissue contiguous with the puncture engages portions of said inner and outer surfaces of said guide member to form a fluid tight interface therebetween;

(d) extending said distal portion of said instrument through at least a portion of said piercing device so that said distal portion of said instrument slides along said inner surface of said guide member and is guided thereby through the percutaneous puncture, whereupon said working means passes therethrough into the internal portion;

(e) sliding said piercing device off of said instrument by passing the instrument between said marginal edges without deforming said distal portion of said instrument to leave said working means within the interior portion of the being's body; and (f) operating said instrument to cause said working means to perform a surgical procedure within the internal portion of the body of the being.

26. The method of claim 25 additionally comprising the step of leaving the instrument in place so that the tissue contiguous with the puncture forms a substantially fluid tight interface with the portion of the instrument extending through the puncture.

27. The method of claim 25 additionally comprising the step of providing said piercing device with a stop surface, and during the formation of the puncture causing the stop surface to engage the surface of the skin of the being so that said piercing tip forms said puncture to have a predetermined depth.

28. The method of claim 25 wherein the portion of the being's body comprises the interior of the abdomen.

29. The method of claim 28 wherein said interior of the abdomen is insufflated when said device is used to form the puncture and when said instrument is extended through the puncture.

30. The method of claim 25 wherein the portion of the being's body comprises the interior of the abdomen.

31. The method of claim 30 wherein said interior of the abdomen is insufflated when said device is used to form the puncture and when said instrument is extended through the puncture.

32. The method of claim 25 additionally comprising the steps of providing another elongated guide member having a longitudinal axis and comprising an elongated trough shaped sidewall having an inner surface, an outer surface, a proximal portion, and a distal end portion, locating said inner surface of said other guide member on the instrument while the instrument is extended through the puncture, sliding said other guide member longitudinally along the instrument so that said distal end portion enters the puncture and into the internal portion, and thereafter sliding the instrument in a proximal direction along said inner surface of said other guide member to remove the instrument from the puncture and leaving said other guide member in place.

33. The method of claim 32 additionally comprising the step of leaving the guide member in place so that the tissue contiguous with the puncture forms a substantially fluid tight interface with the portion of the instrument extending through the puncture.

34. The method of claim 32 additionally comprising the steps of providing another instrument, said other instrument comprising a proximal portion and a distal portion including working means for performing some procedure within the body of said being, sliding said distal portion of said other instrument in a distal direction along said inner surface of said other guide member to be guided thereby through said percutaneous puncture, whereupon said working means passes therethrough into said internal portion.

35. The method of claim 34 additionally comprising the steps of operating the working means of the other instrument from outside the body of the being to perform the procedure.

* * * * *